(12) United States Patent
Dyke et al.

(10) Patent No.: US 9,416,100 B2
(45) Date of Patent: Aug. 16, 2016

(54) PROCESS FOR HYDROGENATING KETONES IN THE PRESENCE OF RU(II) CATALYSTS

(75) Inventors: Alan Dyke, Cambridge (GB); Damian Mark Grainger, Ely (GB); Jonathan Alan Medlock, Basel (CH); Hans Guenter Nedden, Cambridge (GB); Jacques Jean Marie Le Paih, Cambridge (GB); Stephen James Roseblade, Cambridge (GB); Andreas Seger, Soham (GB); Vilvanathan Sivakumar, New Panvel (IN); Antonio Zanotti-Gerosa, Cambridge (GB)

(73) Assignee: Johnson Matthey Public Limited Company, London (GB)

( * ) Notice: Subject to any disclaimer, the term of this patent is extended or adjusted under 35 U.S.C. 154(b) by 584 days.

(21) Appl. No.: 13/257,166

(22) PCT Filed: Mar. 17, 2010

(86) PCT No.: PCT/GB2010/050456
§ 371 (c)(1),
(2), (4) Date: Jan. 27, 2012

(87) PCT Pub. No.: WO2010/106364
PCT Pub. Date: Sep. 23, 2010

(65) Prior Publication Data
US 2012/0123142 A1     May 17, 2012

Related U.S. Application Data

(60) Provisional application No. 61/221,690, filed on Jun. 30, 2009.

(30) Foreign Application Priority Data

Mar. 17, 2009 (GB) .................................. 0904553.5
Jul. 29, 2009 (GB) .................................. 01913166.5

(51) Int. Cl.
| | |
|---|---|
| *C07C 311/05* | (2006.01) |
| *C07C 311/07* | (2006.01) |
| *C07C 311/18* | (2006.01) |
| *C07C 311/20* | (2006.01) |
| *C07F 15/00* | (2006.01) |
| *B01J 31/18* | (2006.01) |
| *B01J 31/22* | (2006.01) |
| *C07C 29/145* | (2006.01) |

(52) U.S. Cl.
CPC ........... *C07C 311/18* (2013.01); *B01J 31/1805* (2013.01); *B01J 31/2295* (2013.01); *C07C 311/05* (2013.01); *C07C 311/07* (2013.01); *C07C 311/20* (2013.01); *C07F 15/0046* (2013.01); *C07F 15/0053* (2013.01); *B01J 2231/643* (2013.01); *B01J 2531/0238* (2013.01); *B01J 2531/821* (2013.01); *C07C 29/145* (2013.01); *C07C 2101/16* (2013.01); *C07C 2523/70* (2013.01); *C07C 2531/18* (2013.01)

(58) Field of Classification Search
CPC .. C07C 311/05; C07C 311/07; C07C 311/18; C07C 311/20; C07F 15/0046; C07F 15/0053
USPC ....................................... 564/94, 98; 556/137
See application file for complete search history.

(56) References Cited

U.S. PATENT DOCUMENTS

| | | | |
|---|---|---|---|
| 7,250,526 B2 | 7/2007 | Blacker et al. | |
| 8,859,815 B2 | 10/2014 | Dominguez et al. | |
| 2007/0225528 A1 | 9/2007 | Noyori et al. | |

FOREIGN PATENT DOCUMENTS

| | | |
|---|---|---|
| CN | 1537088 A | 10/2004 |
| CN | 1926083 A | 3/2007 |
| CN | 101102997 A | 1/2008 |
| JP | 62501068 A | 4/1987 |

(Continued)

OTHER PUBLICATIONS

Hayes et al. J. Am. Chem. Soc. 2005, 127, 7318-7319.*

(Continued)

*Primary Examiner* — Matthew Coughlin
(74) *Attorney, Agent, or Firm* — Reed Smith LLP; Lisa A. Chiarini

(57) ABSTRACT

The present invention relates to a process for hydrogenating a substrate comprising a carbon-heteroatom double bond, the process comprising the step of reacting the substrate with hydrogen gas in the presence of a hydrogenation catalyst, wherein the hydrogenation catalyst is a complex of formula (I): $R_{1-10}$, A and Hal are as defined in the specification. The present invention also provides processes for the preparation of the complex of formula (I) and intermediates thereof.

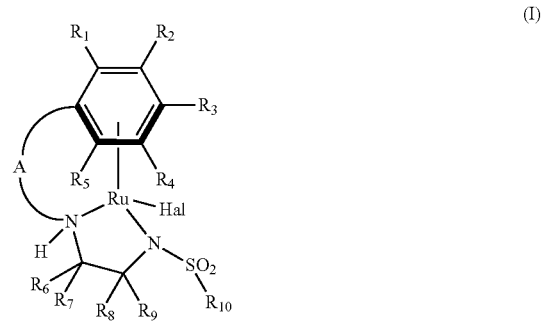

10 Claims, No Drawings

(56) References Cited

FOREIGN PATENT DOCUMENTS

JP 200535961 A 2/2005
WO 8601502 A1 3/1986

OTHER PUBLICATIONS

Supporting Information for Cheung et al. Org. Lett. 2007, 9, 4659-4662, pp. S1-S87.*
Martins et al. Journal of Organometallic Chemistry 2008, 693, 3527-3532.*
Hayes et al., "A Class of Ruthenium(II) Catalyst for Asymmetric Transfer Hydrogenations of Ketones," *J. Am. Chem. Soc.*, 2005, vol. 127, pp. 7318-7319.
Cheung et al., "An Investigation into the Tether Length and Substitution Pattern of Arene- Substituted Complexes for Asymmetric Transfer Hydrogenation of Ketones," *Organic Letters*, 2007, vol. 9, No. 22, pp. 4659-4662.
Morris et al., "The 'Reverse-Tethered' Ruthenium (II) Catalyst for Asymmetric Transfer Hydrogenation: Further Applications," *J. Org. Chem.*, 2006, vol. 71, pp. 7035-7044.
Martins et al., "Further 'tethered' Ru(II) catalysts for asymmetric transfer hydrogenation (ATH) of ketones; the use of a benzylic linker and a cyclohexyldiamine ligand," *Journal of Organometallic Chemistry*, 2008, vol. 693, pp. 3527-3532.
Matharu et al., "A Stereochemically Well-Defined Rhodium(III) Catalyst for Asymmetric Transfer Hydrogenation of Ketones," *Organic Letters*, 2005, vol. 7, No. 24, pp. 5489-5491.
Ohkuma et al., "Asymmetric Hydrogenation of α-Hydroxy Ketones Catalyzed by MsDPEN-Cp*Ir(III) Complex," *Organic Letters*, 2007, vol. 9, No. 13, pp. 2565-2567.
Murata et al., "New Chiral Rhodium and Iridium Complexes with Chiral Diamine Ligands for Asymmetric Transfer Hydrogenation of Aromatic Ketones," *J. Org. Chem.*, 1999, vol. 64, pp. 2186-2187.
Thorpe et al., "Efficient rhodium and iridium-catalysed asymmetric transfer hydrogenation using water-soluble aminosulfonamide ligands," *Tetrahedron Letters*, 2001, vol. 42, pp. 4041-4043.
Gladiali et al., "Asymmetric transfer hydrogenation: chiral ligands and applications," *Chem. Soc. Rev.*, 2006, vol. 35, pp. 226-236.
Parekh et al., "Asymmetric transfer hydrogenation of quinolines using tethered Ru(II) catalysts," *Tetrahedron Asymmetry*, 2010, vol. 21, pp. 1549-1556.
Cheung et al., "Kinetic and structural studies of 'tethered' Ru(II) arene ketone reduction catalysts," *Dalton Trans.*, 2010, vol. 39, pp. 1395-1402.
International Search Report dated May 11, 2011, from PCT International Application No. PCT/GB2010/050456.
British Search Report dated Oct. 12, 2009, from British Patent Application No. 0904553.5.
Morris and Wills, "Asymmetric catalysts for pressure and transfer hydrogenation of ketones," *Chimica Oggi/Chemistry Today*, 2007, vol. 25, No. 2, Catalysis Application Supplement, pp. 11-13.
Chinese Search report dated Jan. 26, 2015, in corresponding Chinese priority application.

\* cited by examiner

PROCESS FOR HYDROGENATING KETONES IN THE PRESENCE OF RU(II) CATALYSTS

CROSS-REFERENCE TO RELATED APPLICATIONS

This application is the U.S. National Phase application of PCT International Application No. PCT/GB20101050456, filed Mar. 17, 2010, and claims priority of British Patent Application No. 0904553.5, filed Mar. 17, 2009; U.S. Provisional Patent Application No. 61/221,690, filed Jun. 30, 2009; and British Patent Application No. 0913166.5, filed Jul. 29, 2009.

FIELD OF THE INVENTION

The present invention relates to a process for catalytically hydrogenating a substrate comprising a carbon-heteroatom double bond. In particular, the present invention relates to catalytically hydrogenating a carbonyl or iminyl compound using a $\eta^6$ arene ruthenium monosulfonated diamine complex.

BACKGROUND OF THE INVENTION

Tethered catalysts have been used in asymmetric transfer hydrogenation reactions (see, for example, Hayes et al, J. Am. Chem. Soc., 2005, 127, 7318, Cheung et al, Organic Letters, 2007, 9(22), 4659, Morris et al, J. Org. Chem., 2006, 71, 7035 and Martins et al, J. Organomet. Chem., 2008, 693, 3527). The transfer hydrogenation conditions utilise formic acid and triethylamine. A hydrogenation reaction differs from a transfer hydrogenation reaction in that hydrogen gas is used and not reagents such as formic acid and triethylamine.

SUMMARY OF THE INVENTION

In one aspect, the invention provides a process for hydrogenating a substrate that includes a carbon-heteroatom double bond. The process includes the step of reacting the substrate with hydrogen gas in the presence of a hydrogenation catalyst, wherein the hydrogenation catalyst is a complex of formula (I):

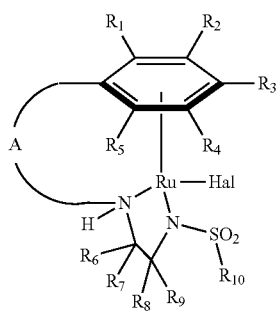

(I)

wherein $R_1$, $R_2$, $R_3$, $R_4$, $R_5$, $R_6$, $R_7$, $R_8$, $R_9$, $R_{10}$, A and Hal are as defined herein.

In another aspect, the invention provides a process for the preparation of a compound of formula (VIII):

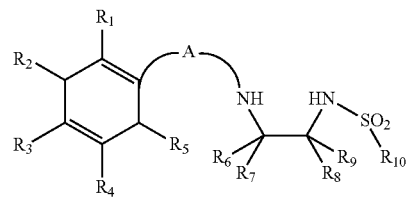

(VIII)

including the steps of:
a) converting a compound of formula (IX) into a compound of formula (X):

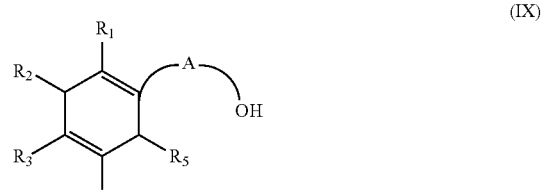

(IX)

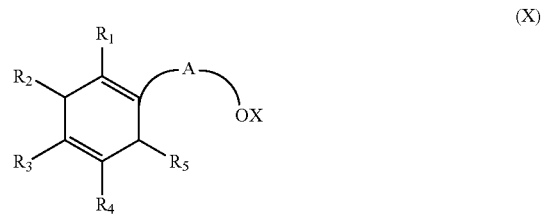

(X)

b) reacting the compound of formula (X) with a compound of formula (XI) in a solvent to form the compound of formula (VIII):

(XI)

wherein $R_1$, $R_2$, $R_3$, $R_4$, $R_5$, $R_6$, $R_7$, $R_8$, $R_9$, $R_{10}$ and A are as defined herein.

In a further aspect, the invention provides a one-pot process for the preparation of a complex of formula (I):

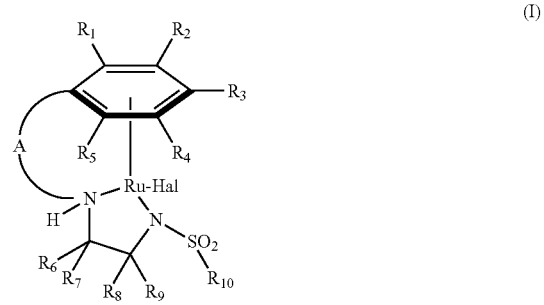

(I)

including the steps of:
i) treating a compound of formula (VIII) with an acid HZ, where Z is an anion

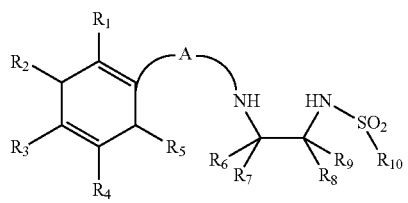
(VIII)

ii) reacting the acid addition salt of the compound of formula (VIII) with a Ru(Hal)$_n$ complex, where Hal is a halogen and n is a number equal to or less than the coordination number of Ru, to form a complex of formula (XIII):

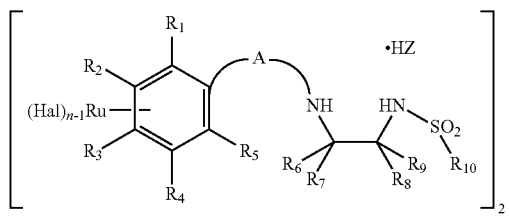
(XIII)

iii) treating the complex of formula (XIII) with a base to form the complex of formula (I):

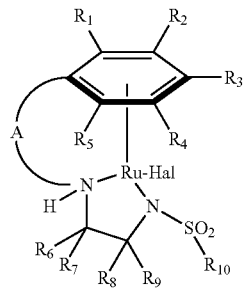
(I)

wherein $R_1$, $R_2$, $R_3$, $R_4$, $R_5$, $R_6$, $R_7$, $R_8$, $R_9$, $R_{10}$ and A are as defined herein.

In yet another aspect, the invention provides a complex selected from the group consisting of:

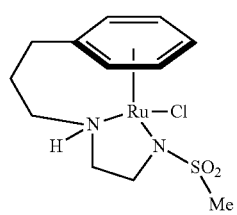
(C)

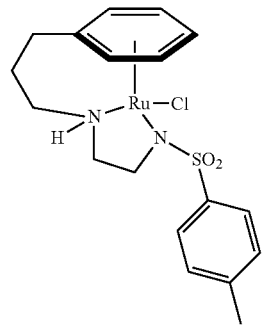
(D)

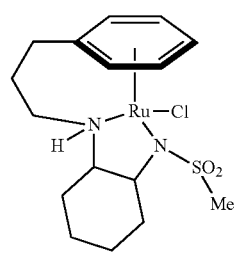
(E)

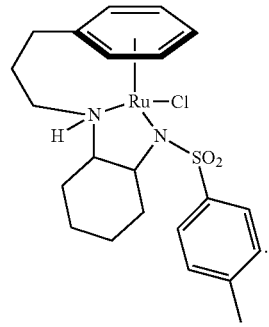
(F)

In a still further aspect, the invention provides a compound, or an acid addition salt thereof, selected from the group consisting of:

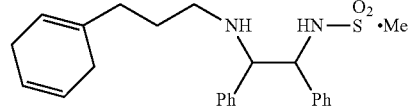
(H)

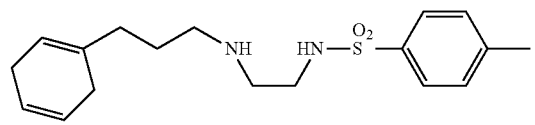
(J)

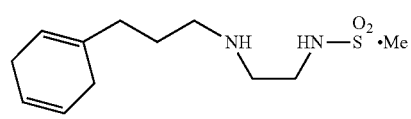
(K)

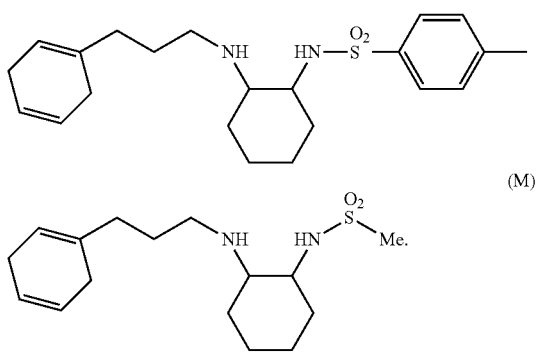

DETAILED DESCRIPTION OF THE INVENTION

Definitions of Terms and Conventions Used

The point of attachment of a moiety or substituent is represented by "-". For example, —OH is attached through the oxygen atom.

"Alkyl" refers to a straight-chain, branched or cyclic saturated hydrocarbon group. In certain embodiments, the alkyl group may have from 1-20 carbon atoms, in certain embodiments from 1-15 carbon atoms, in certain embodiments, 1-10 carbon atoms. The number of carbon atoms is appropriate to the group e.g. a cycloalkyl group must have at least 3 carbon atoms to form a ring. The alkyl group may be unsubstituted or substituted. Unless otherwise specified, the alkyl group may be attached at any suitable carbon atom and, if substituted, may be substituted at any suitable atom. Typical alkyl groups include but are not limited to methyl, ethyl, n-propyl, iso-propyl, cyclopropyl, n-butyl, iso-butyl, sec-butyl, tert-butyl, cyclobutyl, n-pentyl, cyclopentyl, n-hexyl, cyclohexyl and the like.

"Alkoxy" refers to a —O-alkyl group wherein the alkyl group is as described above.

"Alkenyl" refers to a straight-chain, branched or cyclic unsaturated hydrocarbon group having at least one carbon-carbon double bond. The group may be in either the cis- or trans-configuration around each double bond. In certain embodiments, the alkenyl group can have from 2-20 carbon atoms, in certain embodiments from 2-15 carbon atoms, in certain embodiments, 2-10 carbon atoms. The alkenyl group may be unsubstituted or substituted. Unless otherwise specified, the alkenyl group may be attached at any suitable carbon atom and, if substituted, may be substituted at any suitable atom. Examples of alkenyl groups include but are not limited to ethenyl (vinyl), 2-propenyl(allyl), 1-methylethenyl, 2-butenyl, 3-butenyl, cyclobut-1,3-dienyl and the like.

"Alkynyl" refers to a straight-chain, branched or cyclic unsaturated hydrocarbon group having at least one carbon-carbon triple bond. In certain embodiments, the alkynyl group can have from 2-20 carbon atoms, in certain embodiments from 2-15 carbon atoms, in certain embodiments, 2-8 carbon atoms. The number of carbon atoms is appropriate to the group e.g. a cyclic group having at least one carbon-carbon triple bond must have a sufficient number of carbon atoms in order for the cyclic group to be formed. The alkynyl group may be unsubstituted or substituted. Unless otherwise specified, the alkynyl group may be attached at any suitable carbon atom and, if substituted, may be substituted at any suitable atom. Examples of alkynyl groups include, but are not limited to, ethynyl, prop-1-ynyl, prop-2-ynyl, 1-methylprop-2-ynyl, but-1-ynyl, but-2-ynyl, but-3-ynyl and the like.

"Aryl" refers to an aromatic carbocyclic group. The aryl group may have a single ring or multiple condensed rings. In certain embodiments, the aryl group can have from 6-20 carbon atoms, in certain embodiments from 6-15 carbon atoms, in certain embodiments, 6-10 carbon atoms. The aryl group may be unsubstituted or substituted. Unless otherwise specified, the aryl group may be attached at any suitable carbon atom and, if substituted, may be substituted at any suitable atom. Examples of aryl groups include, but are not limited to, phenyl, naphthyl, anthracenyl and the like.

"Aryloxy" refers to an —O-aryl group wherein the aryl group is as described above.

"Hal" refers to a halogen and may be selected from the group consisting of fluorine, chlorine, bromine and iodine.

"Heteroalkyl" refers to a straight-chain, branched or cyclic saturated hydrocarbon group wherein one or more carbon atoms are independently replaced with one or more heteroatoms (e.g. nitrogen, oxygen, phosphorus and/or sulfur atoms). In certain embodiments, the heteroalkyl group may have from 1-20 carbon atoms, in certain embodiments from 1-15 carbon atoms, in certain embodiments, 1-10 carbon atoms. The number of carbon atoms is appropriate to the group e.g. a heterocycloalkyl group must have a sufficient number of carbon atoms together with the heteroatom to form a ring. The heteroalkyl group may be unsubstituted or substituted. Unless otherwise specified, the alkyl group may be attached at any suitable atom and, if substituted, may be substituted at any suitable atom. Examples of heteroalkyl groups include, but are not limited to, ethers, amines, thioethers, epoxide, morpholinyl, piperadinyl, piperazinyl, thirranyl and the like.

"Heteroaryl" refers to an aromatic carbocyclic group wherein one or more carbon atoms are independently replaced with one or more heteroatoms (e.g. nitrogen, oxygen, phosphorus and/or sulfur atoms). In certain embodiments, the heteroaryl group may have from 3-20 carbon atoms, in certain embodiments from 3-15 carbon atoms, in certain embodiments, 3-10 carbon atoms. The heteroaryl group may be unsubstituted or substituted. Unless otherwise specified, the heteroaryl group may be attached at any suitable atom and, if substituted, may be substituted at any suitable atom. Examples of heteroaryl groups include, but are not limited to, furanyl, indolyl, oxazolyl, pyrrolyl, N-methylpyrrolyl, pyridinyl, pyrimidinyl, pyridazinyl, thiazolyl, thiophenyl and the like.

It has been found that a substrate comprising a carbon-heteroatom double bond may be reduced in the presence of hydrogen gas and a tethered $\eta^6$ arene ruthenium monosulfonated diamine complex. In some embodiments, the hydrogenation is asymmetric and the reduced substrate may be obtained in high enantiomeric excess. In some embodiments, when the substrate to be hydrogenated is polyfunctionalised, it has been found that the tethered catalyst is resilient to the presence of the polyfunctional groups and does not become deactivated.

In one aspect, therefore, the present invention provides a process for hydrogenating a substrate comprising a carbon-heteroatom double bond, the process comprising the step of reacting the substrate with hydrogen gas in the presence of a hydrogenation catalyst, wherein the hydrogenation catalyst is a complex of formula (I):

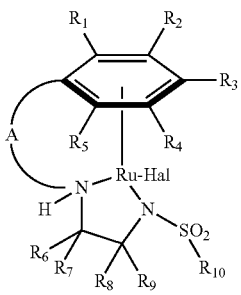

wherein, $R_1$, $R_2$, $R_3$, $R_4$ and $R_5$ are each independently selected from the group consisting of hydrogen, optionally substituted straight, branched or cyclic $C_{1-20}$ alkyl, optionally substituted straight, branched or cyclic $C_{1-20}$ alkoxy, optionally substituted $C_{6-20}$ aryl, optionally substituted $C_{6-20}$ aryloxy, —OH, CN, —$NR_{20}R_{21}$, —COOH, $COOR_{20}$, —$CONH_2$, —$CONR_{20}R_{21}$ and —$CF_3$ wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —$NR_{30}R_{31}$, —$COOR_{30}$, —$CONR_{30}R_{31}$ and —$CF_3$;

$R_1$ and $R_2$, $R_2$ and $R_3$, $R_3$ and $R_4$ or $R_4$ and $R_5$ together form an aromatic ring composed of 6 to 10 carbon atoms which is optionally substituted with one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —$NR_{20}R_{21}$, —$COOR_{20}$, —$CONR_{20}R_{21}$ and —$CF_3$;

$R_6$, $R_7$, $R_8$ and $R_9$ are each independently selected from the group consisting of hydrogen, optionally substituted straight, branched or cyclic $C_{1-20}$ alkyl, optionally substituted straight, branched or cyclic $C_{1-20}$ alkoxy, optionally substituted $C_{6-20}$ aryl and optionally substituted $C_{6-20}$ aryloxy wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —$NR_{20}R_{21}$, —$COOR_{20}$, —$CONR_{20}R_{21}$ and —$CF_3$, or $R_6$ and $R_7$ together with the carbon atom to which they are bound and/or $R_8$ and $R_9$ together with the carbon atom to which they are bound form an optionally substituted $C_{3-20}$ cycloalkyl or an optionally substituted $C_{2-20}$ cycloalkoxy, wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —$NR_{20}R_{21}$, —$COOR_{20}$, —$CONR_{20}R_{21}$ and —$CF_3$, or one of $R_6$ and $R_7$ and one of $R_8$ and $R_9$ together form an optionally substituted $C_{5-10}$ cycloalkyl or an optionally substituted $C_{5-10}$ cycloalkoxy, wherein the substituents are independently selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —$NR_{20}R_{21}$, —$COOR_{20}$, —$CONR_{20}R_{21}$ and —$CF_3$, or $R_{10}$ is an optionally substituted straight, branched or cyclic $C_{1-10}$ alkyl, an optionally substituted $C_{6-10}$ aryl or —$NR_{11}R_{12}$ wherein the substituents are selected from the group consisting of one or more straight, branched or cyclic $C_{1-10}$ alkyl, straight, branched or cyclic $C_{1-10}$ alkoxy, $C_{6-10}$ aryl, $C_{6-10}$ aryloxy, —Hal, —OH, —CN, —$NR_{20}R_{21}$, —$COOR_{20}$, —$CONR_{20}R_{21}$ and —$CF_3$;

$R_{11}$ and $R_{12}$ are independently selected from the group consisting of hydrogen, optionally substituted straight, branched or cyclic $C_{1-10}$ alkyl and optionally substituted $C_{6-10}$ aryl, wherein the substituents are selected from the group consisting of one or more straight, branched or cyclic $C_{1-10}$ alkyl groups, straight, branched or cyclic $C_{1-10}$ alkoxy, $C_{6-10}$ aryl, $C_{6-10}$ aryloxy, —OH, —CN, —$NR_{20}R_{21}$, —$COOR_{20}$, —$CONR_{20}R_{21}$ and —$CF_3$, or $R_{11}$ and $R_{12}$ together with the nitrogen atom to which they are bound form an optionally substituted $C_{2-10}$ cycloalkylamino group, wherein the substituents are selected from the group consisting of one or more straight, branched or cyclic $C_{1-10}$ alkyl, straight, branched or cyclic $C_{1-10}$ alkoxy, $C_{6-10}$ aryl, $C_{6-10}$ aryloxy, —OH, —CN, —$NR_{20}R_{21}$, —$COOR_{20}$, —$CONR_{20}R_{21}$ and —$CF_3$;

$R_{20}$ and $R_{21}$ are independently selected from the group consisting of hydrogen, optionally substituted straight, branched or cyclic $C_{1-20}$ alkyl, optionally substituted straight, branched or cyclic $C_{1-20}$ alkoxy, optionally substituted $C_{6-20}$ aryl, optionally substituted $C_{6-20}$ aryloxy, —OH, —CN, —$NR_{30}R_{31}$, —$COOR_{30}$, —$CONR_{30}R_{31}$ and —$CF_3$, wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN and —$CF_3$;

$R_{30}$ and $R_{31}$ are independently selected from the group consisting of hydrogen, optionally substituted straight, branched or cyclic $C_{1-20}$ alkyl, optionally substituted straight, branched or cyclic $C_{1-20}$ alkoxy, optionally substituted $C_{6-20}$ aryl, optionally substituted $C_{6-20}$ aryloxy, —OH, —CN and —$CF_3$, wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN and —$CF_3$;

A is an optionally substituted straight- or branched-chain $C_{2-5}$ alkyl wherein the substituents are selected from the group consisting of one or more straight, branched or cyclic $C_{1-10}$ alkyl, straight, branched or cyclic $C_{1-10}$ alkoxy, $C_{6-10}$ aryl and $C_{6-10}$ aryloxy, or A is a group of formula (II):

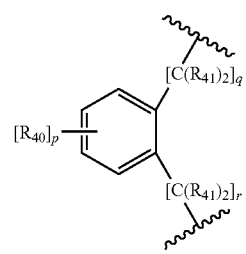

wherein p is an integer selected from 1, 2, 3 or 4;

each $R_{40}$ is independently selected from the group consisting of straight, branched or cyclic $C_{1-20}$ alkyl, straight, branched or cyclic $C_{1-20}$ alkoxy, $C_{6-20}$ aryl, $C_{6-20}$ aryloxy, —OH, —CN or —$CF_3$;

q and r are independently integers selected from 0, 1, 2 or 3 wherein q+r=1, 2 or 3;

each $R_{41}$ is independently selected from the group consisting of hydrogen, straight, branched or cyclic $C_{1-20}$ alkyl, straight, branched or cyclic $C_{1-20}$ alkoxy, $C_{6-20}$ aryl, $C_{6-20}$ aryloxy, —OH, —CN and —$CF_3$; and Hal is a halogen.

The carbon atoms to which $R_6$, $R_7$, $R_8$ and $R_9$ are bound may be asymmetric. The complex of formula (I) therefore may be chiral and the hydrogenation process of the invention an asymmetric hydrogenation process. It is envisaged that chiral catalysts and asymmetric hydrogenation processes are within the scope of the invention.

In one embodiment, the process is suitable for selectively hydrogenating a carbonyl group to provide the corresponding alcohol.

A suitable substrate to be hydrogenated includes, but is not limited to, a carbonyl of formula (III):
wherein,

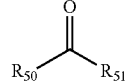

(III)

$R_{50}$ and $R_{51}$ are each independently selected from the group consisting of hydrogen, an optionally substituted straight, branched or cyclic $C_{1-20}$ alkyl, an optionally substituted straight, branched or cyclic $C_{2-20}$ alkenyl, an optionally substituted $C_{2-20}$ alkynyl, an optionally substituted $C_{6-20}$ aryl, an optionally substituted straight, branched or cyclic $C_{1-20}$ heteroalkyl, an optionally substituted $C_{3-20}$ heteroaryl, —$NR_{60}R_{61}$, —$COR_{60}$, —$COOR_{60}$, —$CONR_{60}R_{61}$, an optionally substituted —$C_{1-20}$-alkyl-$COOR_{60}$, an optionally substituted —$C_{1-20}$-alkyl-$COR_{60}$, an optionally substituted —$C_{1-20}$-alkyl-$CONR_{60}R_{61}$, optionally substituted —$C_{2-20}$-alkynyl-$C_{6-20}$-aryl and optionally substituted —$C_{2-20}$ alkynyl-$C_{1-20}$-alkyl; or $R_{50}$ and $R_{51}$ are bound by an optionally substituted $C_{1-20}$ alkyl, an optionally substituted $C_{1-20}$ alkoxy or an optionally substituted $C_{2-20}$ alkenyl; or $R_{50}$ and $R_{51}$ are bound to form a 5, 6 or 7 membered ring by an optionally substituted —$(CH_2)_t$-(ortho-$C_{5-6}$-aryl)-$(CH_2)_u$— chain, an optionally substituted —$(CH_2)_t$-(ortho-$C_{5-6}$-aryl)-Q-$(CH_2)_u$— chain or an optionally substituted —$(CH_2)_t$-(ortho-$C_{5-6}$-heteroaryl)-$(CH_2)_u$— chain, wherein t is an integer selected from 0 or 1,
u is an integer selected from 2, 3 or 4,
Q is selected from the group consisting of —O—, —N— and —$SO_2$—, wherein the substituents are selected from the group consisting of one or more of straight, branched or cyclic $C_{1-20}$ alkyl, straight, branched or cyclic $C_{1-20}$ alkoxy, $C_{6-20}$ aryl, $C_{6-20}$ aryloxy, straight, branched or cyclic $C_{1-20}$ heteroalkyl, $C_{6-20}$ heteroaryl, straight or branched tri-$C_{1-20}$-alkylsilyl-, -Hal, —OH, —CN, —$NR_{60}R_{61}$, —$COR_{60}$, —$COOR_{60}$, —$CONR_{60}R_{61}$ and —$CF_3$, wherein $R_{60}$ and $R_{61}$ are independently selected from the group consisting of hydrogen, straight, branched or cyclic $C_{1-20}$ alkyl, straight, branched or cyclic $C_{1-20}$ alkoxy, $C_{6-20}$ aryl, $C_{6-20}$ aryloxy and —OH.

In one embodiment, when $R_{50}$ and $R_{51}$ are bound to form a 5, 6 or 7 membered ring, Q is preferably —O— or —$SO_2$—. In another embodiment, the substrate to be hydrogenated may be selected from an optionally substituted 1-indanone, an optionally substituted 2-indanone, an optionally substituted α-tetralone, an optionally substituted β-tetralone, an optionally substituted 6,7,8,9-tetrahydro-5-benzocycloheptenone, an optionally substituted 5,7,8,9-tetrahydro-6H-benzo[A]cyclohepten-6-one, an optionally substituted benzofuran-3(2H)-one, an optionally substituted 4-chromanone and an optionally substituted 3,4-dihydro-1-benzoxepin-5(2H)-one. In one embodiment, the substituents are selected from the group consisting of one or more of straight, branched or cyclic $C_{1-20}$ alkyl and —Hal. In another embodiment, the substituents are selected from methyl, ethyl, n-propyl, is-propyl, fluorine, chlorine, bromine and iodine.

In yet another embodiment, the process is suitable for selectively hydrogenating an iminyl group to provide the corresponding amine.

A suitable substrate to be hydrogenated includes, but is not limited to, a compound of formula (IV) or (V):

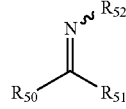

(IV)

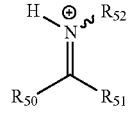

(V)

$R_{50}$ and $R_{51}$ are as described above with regard to the carbonyl of formula (III);

$R_{52}$ is selected from the group consisting of hydrogen, an optionally substituted straight, branched or cyclic $C_{1-20}$ alkyl, straight, branched or cyclic $C_{1-20}$ alkoxy, an optionally substituted straight, branched or cyclic $C_{2-20}$ alkenyl, an optionally substituted $C_{6-20}$ aryl, an optionally substituted $C_{6-20}$ aryloxy, an optionally substituted —$C_{1-20}$-alkyl-$C_{6-20}$-aryl, an optionally substituted straight, branched or cyclic $C_{1-20}$ heteroalkyl, an optionally substituted $C_{3-20}$ heteroaryl, —$NR_{70}R_{71}$, —$COR_{70}$, —$COOR_{70}$, —$CONR_{70}R_{71}$, an optionally substituted —$C_{1-20}$-alkyl-$COOR_{70}$, an optionally substituted —$C_{1-20}$-alkyl-$COR_{70}$, an optionally substituted —$C_{1-20}$-alkyl-$CONR_{70}R_{71}$, —$SOR_{70}$, —$SO_2R_{70}$, —$P(O)(R_{70})_2$, or $R_{52}$ and one of $R_{50}$ and $R_{51}$ are bound to form an optionally substituted $C_{1-20}$-heteroalkyl group, wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, straight, branched or cyclic $C_{1-20}$ heteroalkyl, $C_{6-20}$ heteroaryl, —Hal, —OH, —ON, —$NR_{70}R_{71}$, —$COOR_{70}$, —$CONR_{70}R_{71}$ or —$CF_3$, and wherein $R_{70}$ and $R_{71}$ are independently selected from the group consisting of hydrogen, straight, branched or cyclic $C_{1-20}$ alkyl, straight, branched or cyclic $C_{1-20}$ alkoxy, $C_{6-20}$ aryl, $C_{6-20}$ aryloxy, —OH, —C(O)—($C_{1-20}$-alkyl) and —C(O)O—($C_{1-20}$-alkyl).

When the substrate to be hydrogenated is a compound of formula (V), any suitable anion may be present.

When $R_{50}$, $R_{51}$ and/or $R_{52}$ are different, the compounds of formulae (III), (IV) or (V) are prochiral and the hydrogenation catalysed by the metal complex of formula (I) is enantioselective. The enantiomeric excess is preferably greater than 80% ee. In certain embodiments, the enantiomeric excess is greater than 85% ee, in certain embodiments greater than 90% ee, in certain embodiments greater than 93% ee.

The process according to the invention may be carried out either in the absence of a solvent or in presence of a solvent. In one embodiment therefore the process further comprises a solvent.

Preferably, the solvent comprises water, an alcohol, an aromatic solvent (such as benzene or toluene), an ether (cyclic or open chain, such as tetrahydrofuran (THF) or methyl tert-butylether (MTBE)), an ester (such as ethyl acetate) or a combination thereof. When the solvent comprises an alcohol, preferred alcohols have boiling points at atmospheric pressure (i.e. $1.0135 \times 10^5$ Pa) below 160° C., more preferably below 120° C. and even more preferably below 100° C. Preferred examples are methanol, ethanol, n-propanol, isopropanol, n-butanol or combinations thereof. More preferably, the alcohol is methanol, isopropanol or a combination thereof. Particular preference is given to methanol.

The concentration range of the complex of formula (I) may vary widely. In general, a substrate/complex ratio of about 50,000:1 to about 25:1, preferably from about 2000:1 to about 50:1, more preferably about 1000:1 to about 100:1 can be achieved.

The hydrogenation process may be carried out at typical pressures of about 1 bar to about 100 bar. Advantageously, about 20 bar to about 85 bar and, in particular, about 15 bar to about 35 bar can be used.

The hydrogenation process may be carried out at temperatures between about 0° C. to about 120° C. Suitably, the process can be carried out at about 20° C. to about 80° C. and, most suitably, at about 30° C. to about 60° C.

The process of the present invention may further comprise a silver salt. Without wishing to be bound by theory, it is believed that the silver salt removes the halogen (Hal) from the complex of formula (I) to form a ruthenium complex of formula (VI) and/or formula (VII). It is further believed that suitable silver salts are those which are more soluble than the formed AgHal.

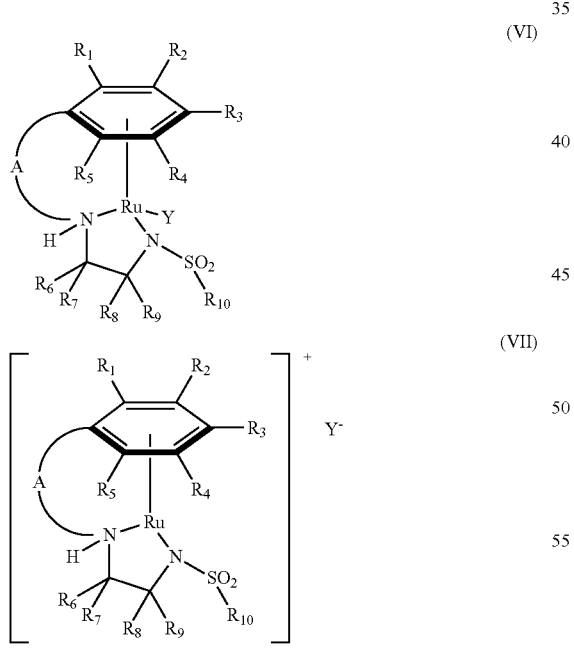

Y is an anion from the silver salt. Preferably, the conjugate acid of the anion Y has a pKa in water below about 4, more preferably below about 2 and most preferably below about 0.

Suitable silver salts include silver perfluorinated alkane-sulfonates (such as silver triflate) or silver (perfluorinated alkanesulfonate)amides. Alternatively, silver hexafluorophosphate, silver tetrafluoroborate or silver perchlorate can be used. The silver salt may be present in any suitable mol %, for example, from about 0.2 to 500 mol % to the amount of ruthenium complex used.

In another embodiment, the process of the present invention may further comprise a fluorinated sulfonic acid, preferably trifluoromethanesulfonic acid. The fluorinated sulfonic acid may be used in any suitable mol %, for example, 2 mol %.

Examples of anion Y therefore may include, but are not limited to, trifluoromethanesulphonate, tetrafluoroborate, hexafluorophosphate and perchlorate.

The ruthenium catalyst and the substrate, as well as the solvent and/or additive if present, can be mixed in any suitable order before the hydrogen gas is applied to the reaction mixture.

The hydrogenation process may be carried out for any suitable period of time and this period of time will depend upon the reaction conditions under which the hydrogenation is conducted e.g. substrate concentration, catalyst concentration, pressure, temperature and the like. Once the hydrogenation process has been determined to be complete, the product may be isolated and purified using conventional techniques.

In one embodiment, the hydrogenation catalyst is metal complex of formula (I):

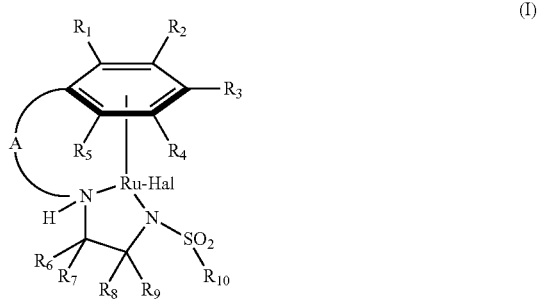

wherein $R_1$, $R_2$, $R_3$, $R_4$ and $R_5$ are each independently selected from the group consisting of hydrogen, straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —$NR_{20}R_{21}$, —COOH, $COOR_{20}$, —$CONH_2$, —$CONR_{20}R_{21}$ and —$CF_3$. In another embodiment, $R_1$, $R_2$, $R_3$, $R_4$ and $R_5$ are each independently selected from the group consisting of hydrogen, straight- or branched-chain $C_{1-10}$ alkyl, straight- or branched-chain $C_{1-10}$ alkoxy, $C_{6-10}$ aryl, $C_{6-10}$ aryloxy and —OH. Preferably, $R_1$, $R_2$, $R_3$, $R_4$ and $R_5$ are each independently selected from the group consisting of hydrogen, straight-chain $C_{1-10}$ alkyl and branched-chain $C_{1-10}$ alkyl. More preferably, $R_1$, $R_2$, $R_3$, $R_4$ and $R_5$ are each independently selected from the group consisting of hydrogen, methyl, ethyl, n-propyl, i-propyl, n-butyl, i-butyl, s-butyl and t-butyl. Particular preference is given to $R_1$, $R_2$, $R_3$, $R_4$ and $R_5$ each being hydrogen.

In yet another embodiment, $R_6$, $R_7$, $R_8$ and $R_9$ are each independently selected from the group consisting of hydrogen, optionally substituted straight- or branched-chain $C_{1-10}$ alkyl, optionally substituted straight- or branched-chain $C_{1-10}$ alkoxy, optionally substituted $C_{6-10}$ aryl and optionally substituted $C_{6-10}$ aryloxy wherein the substituents are selected from the group consisting of straight- or branched-chain $C_{1-10}$ alkyl, straight- or branched-chain $C_{1-10}$ alkoxy, $C_{6-10}$ aryl, $C_{6-10}$ aryloxy and —OH. The groups $R_6$, $R_7$, $R_8$ and $R_9$ are preferably each independently selected from the group consisting of hydrogen and optionally substituted $C_{6-10}$ aryl. Preferably, $R_6$, $R_7$, $R_8$ and $R_9$ are each independently selected from the group consisting of hydrogen or phenyl. Preferably, one of $R_6$ and $R_7$ is phenyl and the other of $R_6$ and $R_7$ is hydrogen. Preferably, one of $R_8$ and $R_9$ is phenyl and the other of $R_8$ and $R_9$ is hydrogen.

In one embodiment, $R_6$, $R_7$, $R_8$ and $R_9$ are each hydrogen.

In another embodiment, $R_6$ and $R_7$ together with the carbon atom to which they are bound and/or $R_8$ and $R_9$ together with the carbon atom to which they are bound form an optionally substituted $C_{5-10}$ cycloalkyl or an optionally substituted $C_{5-10}$ cycloalkoxy, wherein the substituents are selected from the group consisting of straight- or branched-chain $C_{1-10}$, straight- or branched-chain $C_{1-10}$ alkoxy, $C_{6-10}$ aryl, $C_{6-10}$ aryloxy and —OH.

In yet another embodiment, one of $R_6$ and $R_7$ and one of $R_8$ and $R_9$ together form an optionally substituted $C_{5-10}$ cycloalkyl or an optionally substituted $C_{5-10}$ cycloalkoxy, wherein the substituents are selected from the group consisting of straight- or branched-chain $C_{1-10}$ alkyl, straight- or branched-chain $C_{1-10}$ alkoxy, $C_{6-10}$ aryl, $C_{6-10}$ aryloxy and —OH.

In yet another embodiment, $R_{10}$ is an optionally substituted straight, branched or cyclic $C_{1-10}$ alkyl, an optionally substituted $C_{6-10}$ aryl wherein the substituents are selected from the group consisting of one or more straight, branched or cyclic $C_{1-10}$ alkyl, straight, branched or cyclic $C_{1-10}$ alkoxy, $C_{6-10}$ aryl, $C_{6-10}$ aryloxy, —Hal, —OH, —CN, —$NR_{20}R_{21}$, —$COOR_{20}$, —$CONR_{20}R_{21}$ and —$CF_3$. In another embodiment, the substituents are selected from the group consisting of one or more straight, branched or cyclic $C_{1-10}$ alkyl, straight, branched or cyclic $C_{1-10}$ alkoxy, $C_{6-10}$ aryl, $C_{6-10}$ aryloxy, —Hal, or —$CF_3$. In another embodiment, $R_{10}$ is a straight- or branched-chain $C_{1-10}$ alkyl or a $C_{6-10}$ aryl optionally substituted with one or more straight- or branched-chain $C_{1-10}$ alkyl groups. Examples of $R_{10}$ include, but are not limited to, p-tolyl, methyl, p-methoxyphenyl, p-chlorophenyl, trifluoromethyl, 3,5-dimethylphenyl, 2,4,6-trimethylphenyl, 2,4,6-triisopropylphenyl, 4-tert-butylphenyl, pentamethylphenyl and 2-naphthyl. Preferably, $R_{10}$ is methyl or a tolyl group.

In another embodiment, $R_{10}$ is —$NR_{11}R_{12}$ wherein $R_{11}$ and $R_{12}$ are independently selected from the group consisting of straight- or branched-chain $C_{1-10}$ alkyl and $C_{6-10}$ aryl optionally substituted with one or more straight- or branched-chain $C_{1-10}$ alkyl groups.

In yet another embodiment, $R_{11}$ and $R_{12}$ together with the nitrogen atom to which they are bound form an optionally substituted $C_{5-10}$ cycloalkyl-amino group wherein the substituents are selected from the group consisting of straight- or branched-chain $C_{1-10}$ alkyl, straight- or branched-chain $C_{1-10}$ alkoxy, $C_{6-10}$ aryl, $C_{6-10}$ aryloxy and —OH.

In one embodiment, A is an optionally substituted straight- or branched-chain $C_{2-5}$ alkyl, preferably an optionally substituted straight- or branched-chain $C_{3-5}$ alkyl, wherein the substituents are selected from the group consisting of straight- or branched-chain $C_{1-10}$ alkyl, straight- or branched-chain $C_{1-10}$ alkoxy, $C_{6-10}$ aryl and $C_{6-10}$ aryloxy. Preferably, A is —$(CH_2)_2$—, —$(CH_2)_3$—, —$(CH_2)_4$— or —$(CH_2)_5$—. Particular preference is given to —$(CH_2)_3$— or —$(CH_2)_4$—.

Alternatively, A can be a group of formula (II) i.e. the —$[C(R_{41})_2]_q$— and —$[C(R_{41})_2]_r$— groups are ortho to each other.

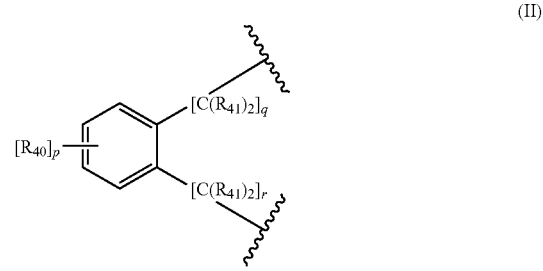
(II)

wherein p is an integer selected from 1, 2, 3 or 4;

each $R_{40}$ is independently selected from the group consisting of straight, branched or cyclic $C_{1-20}$ alkyl, straight, branched or cyclic $C_{1-20}$ alkoxy, $C_{6-20}$ aryl, $C_{6-20}$ aryloxy, —OH, —CN or —$CF_3$;

q and r are independently integers selected from 0, 1, 2 or 3 wherein q+r=1, 2 or 3; and each $R_{41}$ is independently selected from the group consisting of hydrogen, straight, branched or cyclic $C_{1-20}$ alkyl, straight, branched or cyclic $C_{1-20}$ alkoxy, $C_{6-20}$ aryl, $C_{6-20}$ aryloxy, —OH, —CN or —$CF_3$.

In one embodiment, p is 0. The phenyl ring therefore is not substituted by any $R_{40}$ groups.

In another embodiment, each $R_{41}$ are independently selected from the group consisting of hydrogen, straight-chain $C_{1-10}$ alkyl and branched-chain $C_{1-10}$ alkyl. More preferably, each $R_{41}$ are each independently selected from the group consisting of hydrogen, methyl, ethyl, n-propyl, i-propyl, n-butyl, i-butyl, s-butyl and t-butyl. Particular preference is given to each $R_{41}$ being hydrogen.

Examples of A include, but are not limited to, the following:

(IIa)

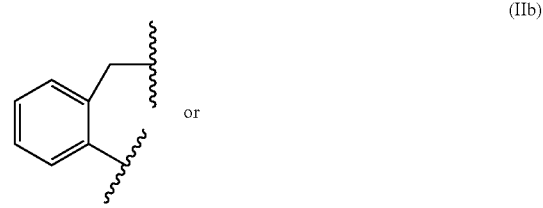
(IIb)

or

(IIc)

In one embodiment, Hal is chlorine, bromine or iodine, preferably chlorine.

Preferred metal complexes of formula (I) are shown below:
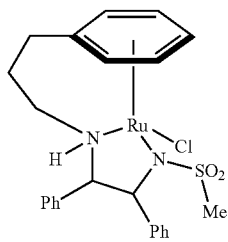
[Ms-DPEN Teth Ru Cl]
(A)
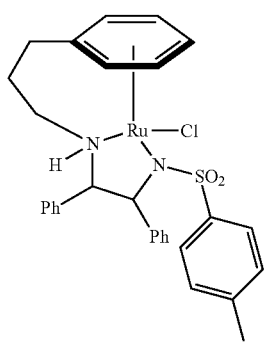
[Ts-DPEN Teth Ru Cl]
(B)
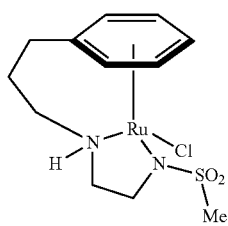
[Ms-EN Teth Ru Cl]
(C)
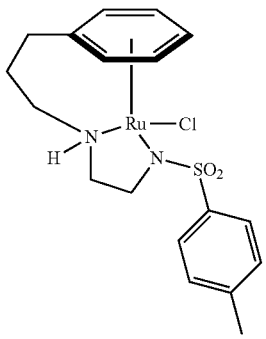
[Ts-EN Teth Ru Cl]
(D)
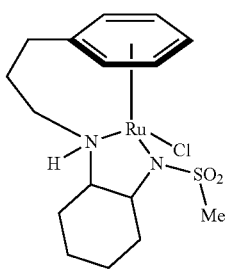
[Ms-DACH Teth Ru Cl]
(E)
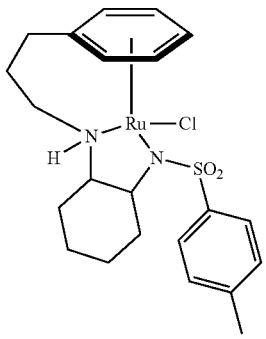
[Ts-DACH Teth Ru Cl]
(F)
Complex (B) may be prepared according to Wills et al, J. Am. Chem. Soc., 2005, 127(20), 7318. The Wills method involves five steps:
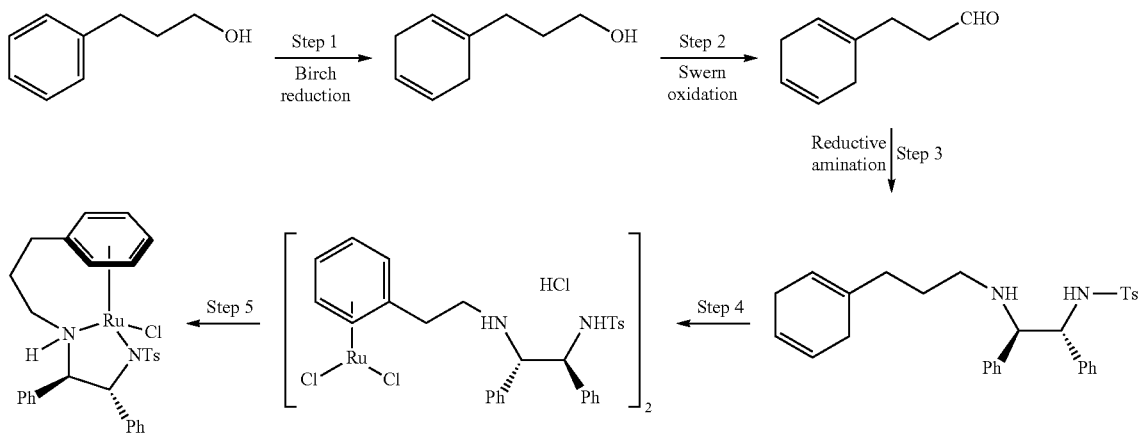

Step 1 is a Birch reduction of 3-phenyl-propanol to 3-cyclohexa-1,4-dienyl-propan-1-ol. Step 2 involves a Swern oxidation of 3-cyclohexa-1,4-dienyl-propan-1-ol to produce 3-cyclohexa-1,4-dienyl-propionaldehyde. This stage is disadvantageous as a change in oxidation state occurs and, for the subsequent reduction, the reagent lithium aluminium hydride is used which is unsuitable for larger scale reactions. Step 3 is a reductive amination reaction to form the desired (R,R)-TsDPEN. However, a by-product is also formed during the course of the reductive amination which complicates the subsequent purification of (R,R)-TsDPEN. Steps 4 and 5 relate to the synthesis of the ruthenium dimer and monomer respectively.

The inventors of the present case have overcome the above disadvantages to provide an improved process for the preparation of the complexes of formula (I).

The present invention therefore provides a process for the preparation of a compound of formula (VIII):

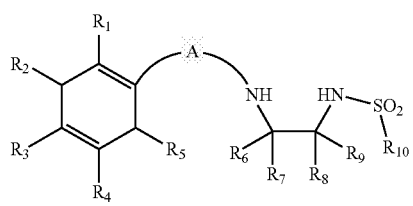
(VIII)

comprising the steps of:
(a) converting a compound of formula (IX) into a compound of formula (X):

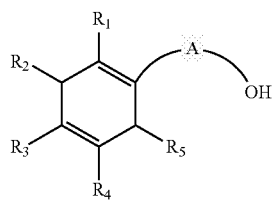
(IX)

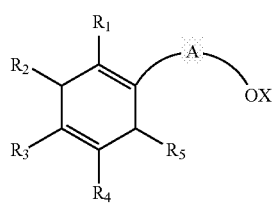
(X)

(b) reacting the compound of formula (X) with a compound of formula (XI) in a solvent to form the compound of formula (VIII):

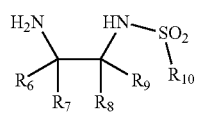
(XI)

wherein $R_1$, $R_2$, $R_3$, $R_4$, $R_5$, $R_6$, $R_7$, $R_8$, $R_9$, $R_{10}$ and A are as defined above, and X is an electrophilic group.

The process of the invention provides a process for the production of a compound of formula (VIII) which does not involve a change in oxidation state. Moreover, a reductive amination step is not required and, as such, the use of lithium aluminium hydride is avoided. This means that the process of the invention is suitable for large scale manufacturing procedures.

Step (a) preferably comprises reacting the compound of formula (IX) with a base and a compound of formula (XII):

X-LG   (XII)

wherein LG is a leaving group.

The base is preferably an amine, for example, lutidine or triethylamine. Desirably, the reaction is carried out under an inert atmosphere (such as nitrogen or argon). Suitably, a solvent may be used, for example, any suitable aprotic polar solvent (such as, dichloromethane). The solvent may be anhydrous, although this is not essential.

The compound of formula (IX), the base, the solvent and the compound of formula (XII) may be added in any suitable order. In a preferred process of the invention, however, the compound of formula (IX) and the base is placed in a reaction vessel, together with the solvent, and then the compound of formula (XII) is added.

The compound of formula (XII) may also be present as a solution in a solvent. In this case, the solvent may be any suitable polar aprotic solvent (such as dichloromethane). The solvent may the same or different to the solvent used to prepare the reaction mixture of the compound of formula (XII) and the base, although in a preferred embodiment of the invention, the solvents are the same.

The compound of formula (XII) is preferably selected from the group consisting of trifluoromethane sulfonic anhydride, trifluoromethane sulfonic acid, methanesulfonyl chloride and p-toluenesulfonyl chloride. X therefore may be —$SO_2CF_3$ (for trifluoromethane sulfonic anhydride and trifluoromethane sulfonic acid), —$SO_2Me$ (for methanesulfonyl chloride) or —$SO_2$—$C_6H_4$-p-$CH_3$ (for p-toluenesulfonyl chloride). In these instances, LG may be —O—$SO_2CF_3$ (for trifluoromethane sulfonic anhydride), —OH (for trifluoromethane sulfonic acid) or —Cl (for methanesulfonyl chloride or p-toluenesulfonyl chloride).

While the compound of formula (XII) is added to the reaction mixture, it is preferred that the temperature range of the reaction is maintained at one or more temperatures between about −10° C. to about 35° C. In a preferred embodiment, the reaction mixture is maintained at a temperature of less than about 5° C. In order to keep the temperature of the reaction mixture within these ranges, the compound of formula (XII) together with the solvent (if used) may be added slowly over a period of time.

The reaction may be continued for a period of from about 30 minutes to about 72 hours, preferably 30 minutes to about 24 hours. During this time, the reaction temperature may be varied one or more times between about −10° C. and about 25° C. If desired, on completion of the reaction, the compound of formula (X) may be separated from the reaction mixture by any appropriate method. Alternatively, the reaction mixture comprising the compound of formula (X) may be used directly without isolation in step (b) of the process of the invention.

In step (b), the compound of formula (X) is reacted with the compound of formula (XI) in a solvent to form the compound of formula (VIII).

In one embodiment, the compound of formula (VIII) is the compound of formula (G):

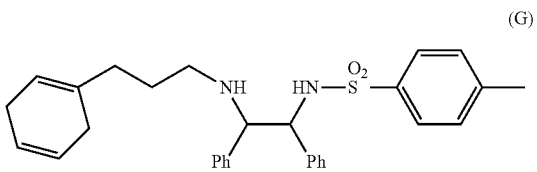 [SMILES: Cc1ccc(S(=O)(=O)NC(c2ccccc2)C(NCCCC2=CCC=CC2)c2ccccc2)cc1]
(G)

In another embodiment, the compound of formula (VIII) is selected from the group consisting of:

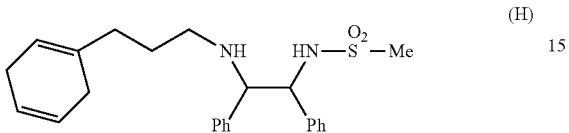
(H)

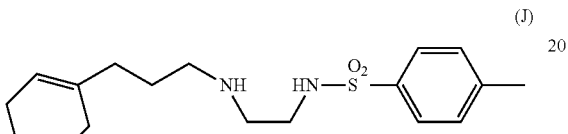
(J)

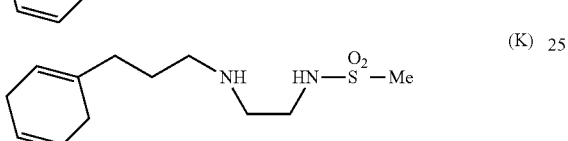
(K)

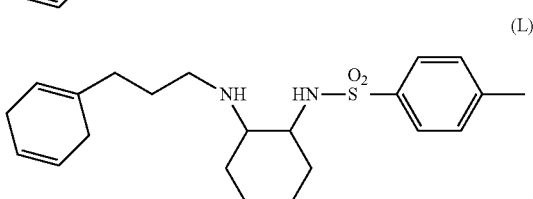
(L)

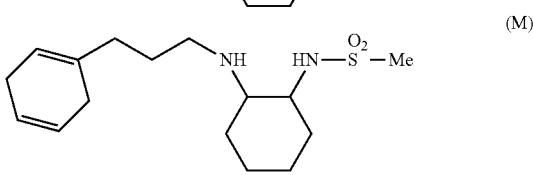
(M)

The compounds of formulae (G), (H), (L) and (M) may be present as enantiomers or diastereoisomers. It is envisaged that enantiomers and diastereoisomers are within the scope of the invention.

Desirably, the reaction is carried out under an inert atmosphere (such as nitrogen or argon). Desirably, a suitable solvent is used, for example, an aprotic polar solvent (such as dichloromethane or 1,2-dimethoxy ethane). The solvent may be anhydrous, although this is not essential. The reaction is preferably carried out at one or more temperatures in the range of between about −10° C. to about 65° C.

Step (b) preferably further comprises a base. More preferably, the base is an amine, for example, triethylamine.

The compound of formula (X), the compound of formula (XI), the base (if used) and the solvent may be added in any suitable order. In one embodiment, the compound of formula (XI) is placed in a reaction vessel, together with the solvent and the base (if used), heated if necessary and the compound of formula (X) added, either alone or as a solution in solvent. Alternatively, the compound of formula (X) and the solvent may be present in a reaction vessel, cooled or heated if necessary and then the compound of formula (XI), the base (if used) and the solvent may be added.

The reaction may be continued for a period of from about 30 minutes to about 24 hours. During this time, the reaction temperature may be varied one or more times between about −10° C. and about 100° C., preferably between about 0° C. and about 85° C. On completion of the reaction, the compound of formula (VIII) may be separated from the reaction mixture by any appropriate method and if necessary purified.

Preferably, the process of the invention further comprises the steps of:
c) treating the compound of formula (VIII) with an acid HZ, where Z is an anion; and
d) reacting the acid addition salt of the compound of formula (VIII) with a Ru(Hal)$_n$ complex, where Hal is a halogen and n is a number equal to or less than the coordination number of Ru, to form a complex of formula (XIII):

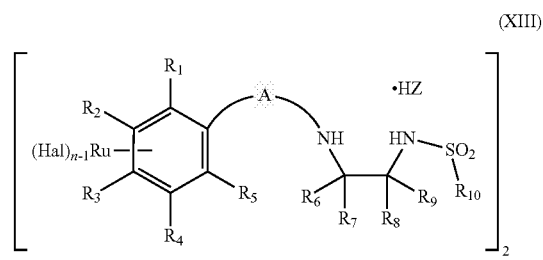
(XIII)

Step c) is preferably carried out in the presence of a solvent. The solvent may be any suitable solvent, for example, a polar protic solvent (such as water, methanol, ethanol, n-propanol or isopropanol), a polar aprotic solvent (such as dichloromethane or dichloroethane) or an aromatic hydrocarbon (such as toluene). Preferably, the solvent is selected from the group consisting of at least one of water, ethanol, isopropanol, dichloroethane and toluene.

Preferably, the acid HZ is selected from the group consisting of hydrochloric acid, hydrobromic acid and hydroiodic acid. More preferably, the acid is hydrochloric acid. Z therefore may be a chloride, bromide or iodide anion, preferably a chloride anion. In a preferred embodiment, the acid HZ is a concentrated aqueous acid.

The halogen Hal is preferably selected from the group consisting of chlorine, bromine and iodine. In a preferred embodiment, Ru(Hal)$_n$ is RuCl$_3$, for example, RuCl$_3$.H$_2$O or an aqueous solution of RuCl$_3$, including coordination complexes of RuCl$_3$ such as [RuCl$_3$.(H$_2$O)$_3$], [RuCl$_2$.(H$_2$O)$_4$]Cl etc. n therefore is 3. There is a commercial advantage in using an aqueous solution of RuCl$_3$ in that it is much cheaper than the isolated complex RuCl$_3$.

In one embodiment, the acid addition salt of the compound of formula (VIII) is isolated before reaction with the Ru(Hal)$_n$ complex.

In another embodiment, the acid addition salt of the compound of formula (VIII) is prepared in situ before reaction with the Ru(Hal)$_n$ complex. In this case, it is desirable that the solution of the acid addition salt of the compound of formula (VIII) is warmed to one or more temperatures in the range from about 50° C. to about 80° C. and more preferably about 50° C. to about 75° C. before the addition of the Ru(Hal)$_n$ complex.

The Ru(Hal)$_n$ complex may added as a solution or a suspension in a solvent. The solvent may be any suitable solvent, for example, a polar protic solvent (such as water, methanol, ethanol, n-propanol or isopropanol), a polar aprotic solvent (such as dichloromethane or dichloroethane) or an aromatic hydrocarbon (such as toluene). Preferably, the solvent is selected from the group consisting of at least one of water, ethanol, isopropanol, dichloroethane and toluene. The solvent or solvent mixture may be the same or different to the solvent used in step c).

The reaction is preferably carried out at a temperature in the range from about 50° C. to about 100° C. and more preferably about 50° C. to about 85° C. It is preferred that the reaction temperature is maintained below the decomposition temperatures of the $RuL_n$ and the complex of formula (XIII). As such, when it is known that $RuL_n$ or the complex of formula (XIII) decompose within the temperature ranges given above, the reaction temperature should be maintained below the decomposition temperatures.

Preferably, the compound of formula (VIII) is present in the reaction mixture in stoichiometric excess. Preferably the amount of the compound of formula (VIII) in the reaction mixture is calculated to provide a molar excess of at least 5% over the amount required for the stoichiometric reaction, more preferably an excess of at least 9%.

The reactants may be added in any suitable order, but in a preferred process of the invention the diluted aqueous solution of the $Ru(Hal)_n$ complex is added to the solution of the acid addition salt of the compound of formula (VIII). It is desirable that the diluted aqueous solution of the $Ru(Hal)_n$ complex is added to the solution of the acid addition salt of the compound of formula (VIII) slowly in order to avoid an uncontrollable exotherm.

The reaction may be carried out for a period from about 30 minutes to about 24 hours. On completion, the complex of formula (XIII) may be isolated from the reaction mixture. In this case, the complex is separated by any appropriate method which is dependent on the physical form of the product. Purification of the complex of formula (XIII) is not normally required, although if necessary it is possible to purify the complex using conventional procedures.

Alternatively, it may be desirable to prepare the complex of formula (XIII) in situ.

Preferably, the present invention further comprises the step of treating the complex of formula (XIII) with a base to form the complex of formula (I):

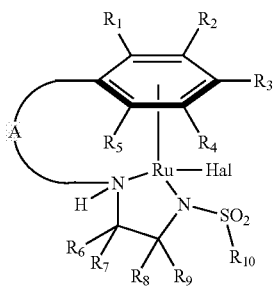
(I)

The complex of formula (XIII) is preferably present in a solvent. The solvent may be any suitable solvent, for example, a polar protic solvent (such as methanol, ethanol, n-propanol or isopropanol), a polar aprotic solvent (such as dichloromethane or dichloroethane) or an aromatic hydrocarbon (such as toluene). Preferably, the solvent is selected from the group consisting of at least one of ethanol, isopropanol, dichloromethane, dichloroethane and toluene. The solvent or solvent mixture may be the same or different to the solvents used in step c) and/or step d).

The base is preferably an amine, for example, triethylamine or N,N-diisopropylamine. In a preferred embodiment, the base is N,N-diisopropylamine.

The reaction may be continued for a period of from about 20 minutes to about 24 hours. During this time, the reaction temperature may be varied one or more times between about −10° C. and about 100° C., preferably between about 0° C. and about 85° C. It is preferred that the reaction temperature is maintained below the decomposition temperature of the complex of formula (I). As such, when it is known that the complex of formula (I) decomposes within the temperature ranges given above, the reaction temperature should be maintained below the decomposition temperature.

On completion of the reaction, the compound of formula (VIII) may be separated from the reaction mixture by any appropriate method which is dependent on the physical form of the product. In particular, solid complexes may be recovered by filtering, decanting or centrifuging. If purification is necessary, the complexes may be obtained in high purity by conventional methods.

In another aspect, the present invention provides a one-pot process for the preparation of a complex of formula (I):

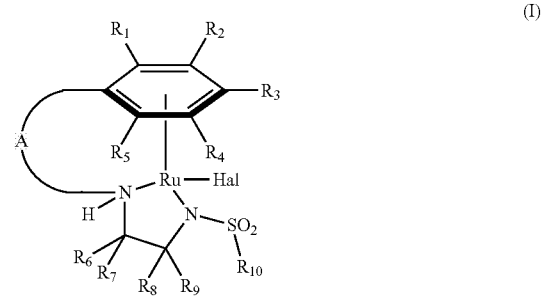
(I)

comprising the steps of:
i) treating a compound of formula (VIII) with an acid HZ, where Z is an anion

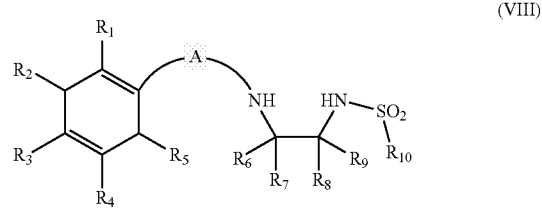
(VIII)

ii) reacting the acid addition salt of the compound of formula (VIII) with a $Ru(Hal)_n$ complex, where Hal is a halogen and n is a number equal to or less than the coordination number of Ru, to form a complex of formula (XIII):

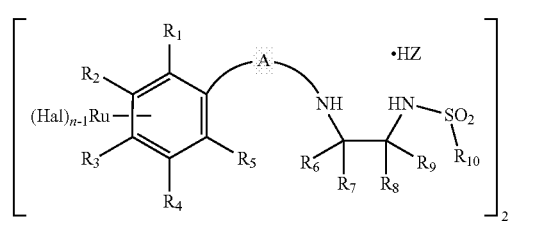
(XIII)

iii) treating the complex of formula (XIII) with a base to form the complex of formula (I):

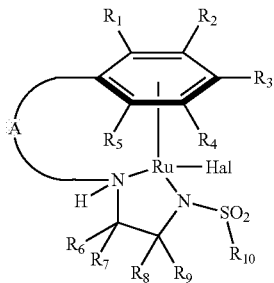
(I)

wherein $R_1, R_2, R_3, R_4, R_5, R_6, R_7, R_8, R_9, R_{10}$ and A are as defined above, and wherein the acid addition salt of the compound of formula (VIII) and the complex of formula (XIII) are prepared in situ.

In yet another aspect, the present invention provides a complex of formula (I) or formula (XIII):

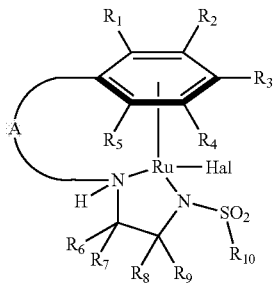
(I)

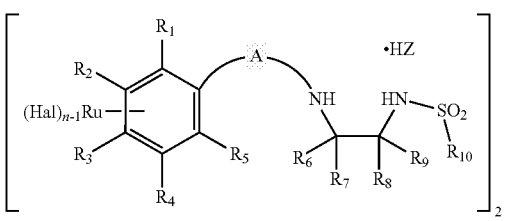
(XIII)

wherein $R_1, R_2, R_3, R_4, R_5, R_6, R_7, R_8, R_9$ and $R_{10}$, A, Hal and Z are as defined above, provided that the complex of formula (I) is not:

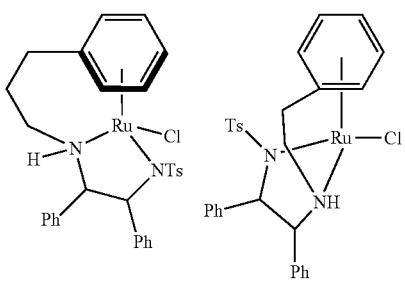

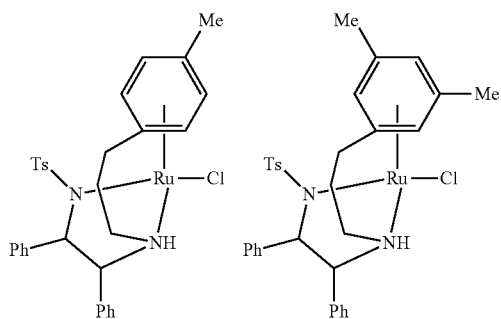

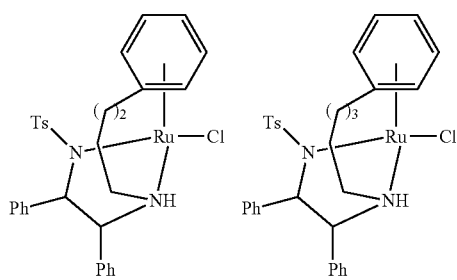

and the complex of formula (XIII) is not:

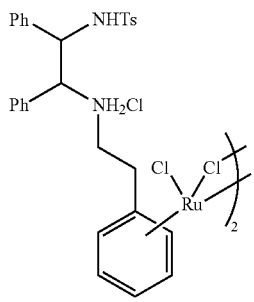

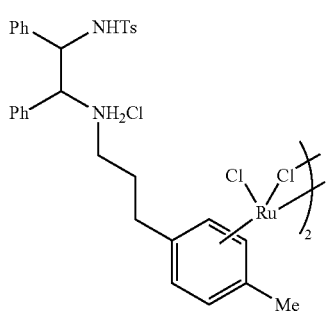

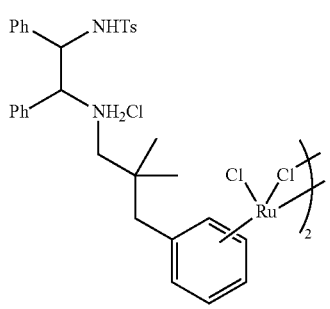

-continued

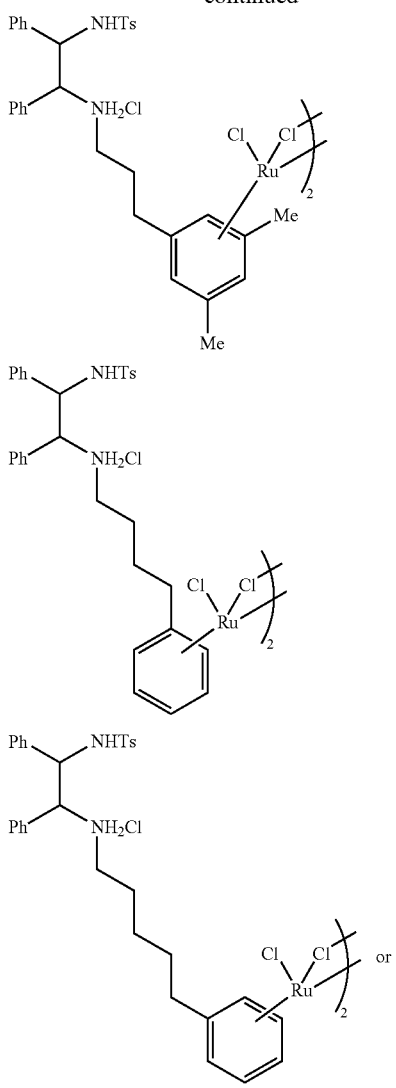

Preferably, the complex of formula (I) selected from the group consisting of:

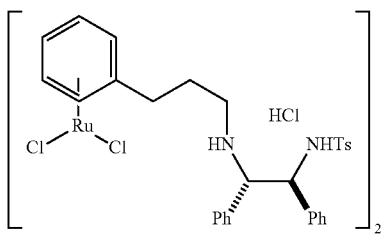

(C)

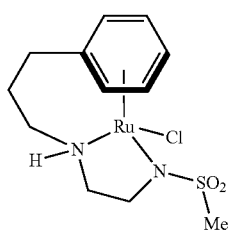

-continued

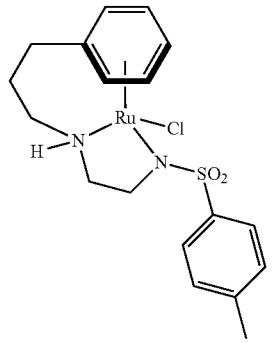

(D)

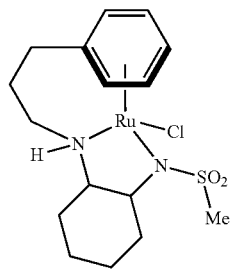

(E)

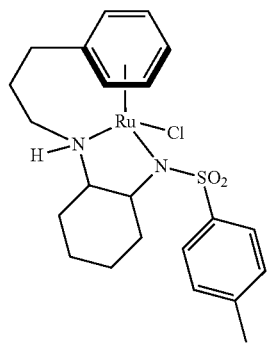

(F)

In another aspect, the present invention provides a compound of formula (VIII), or an acid addition salt thereof,

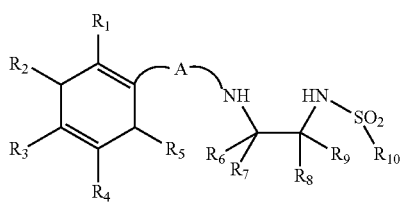

(VIII)

wherein $R_1$, $R_2$, $R_3$, $R_4$, $R_5$, $R_6$, $R_7$, $R_8$, $R_9$, $R_{10}$ and A are as defined above, provided that the compound of formula (VIII) is not:

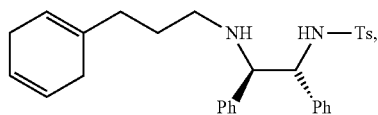

or the hydrogen chloride salt thereof,
or

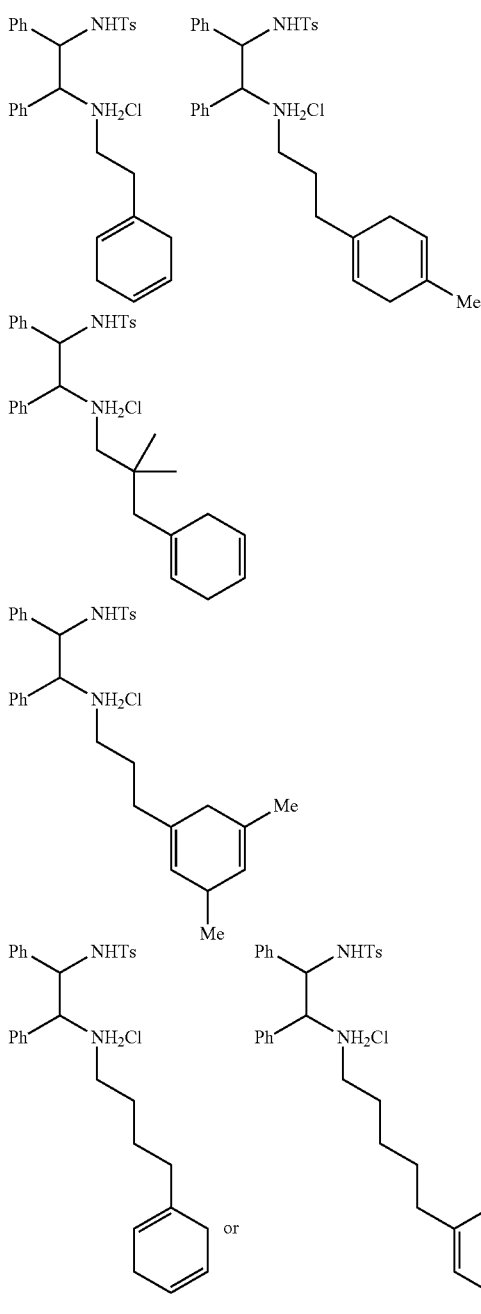

Preferably, the compound of formula (VIII), or an acid addition salt thereof, is selected from the group consisting of:

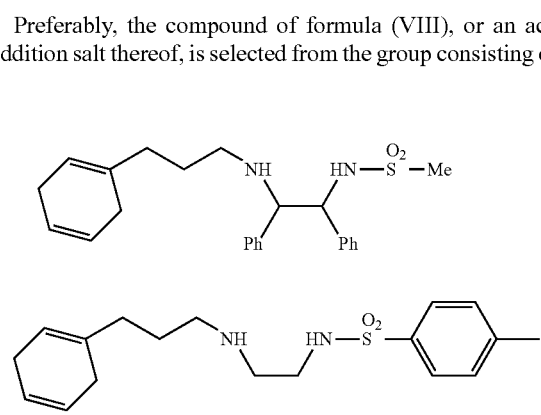

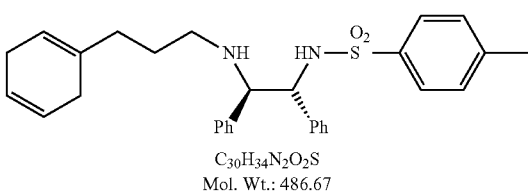

The invention is further illustrated by reference to the following non-limiting Examples.

EXAMPLE 1

Birch Reduction of 3-Phenyl-Propanol

Ammonia is condensed in a round-bottomed flack with four necks (thermometer, a cold finger connected to ammonia lecture bottle, argon inlet with silicone oil bubbler, inlet closed with a stopper). The cold finger is cooled with dry ice and the flask is cooled in a dry ice-EtOH bath. When between 50 and 100 mL of ammonia have been collected (a slow flow of argon is maintained throughout the reaction), 3-phenyl-propanol (5.0 g, MW 136.2, 36.7 mmol) in EtOH (20 mL) are added. Portions of lithium wire are added (~1.0 g) so that the reaction is maintained dark green. After 2 hours at −78° C., the reaction is allowed to warm up to room temperature and the ammonia to evaporate. The reaction is then quenched with a saturated solution of ammonium chloride (200 mL) and extracted with dichloromethane (2×200 mL). The combined dichloromethane fractions are washed with 200 mL of HCl 2N, then dried over $Na_2SO_4$. The solvent is removed at the rotavapor to give a clear colourless oil (4.77 g, 95% yield). Purity is determined by $^1H$ NMR.

EXAMPLE 2

Synthesis of Tethered (R,R)-TsDPEN

A solution of 3-(1,4-cyclohexadien-1-yl)-1-propanol (MW: 138.21; 22.1 g, 0.16 mol, 1.6 eq.) and 2,6-lutidine (MW: 107.16, d: 0.92 g/ml; 24.5 ml, 0.21 mol, 2.10 eq.) in anhydrous $CH_2Cl_2$ (500 ml) was cooled to 0° C. under $N_2$. A solution of triflic anhydride (MW: 281.14, d: 1.677; 29.1 ml, 0.17 mol, 1.7 eq.) in anhydrous $CH_2Cl_2$ (100 ml) was added slowly, keeping the internal temperature below 5° C. The resulting amber solution was stirred for 30 min at 0° C., 60 min at room temperature, and cooled back to 0° C. A solution of (R,R)-TsDPEN (MW: 366.48; 36.6 g, 0.10 mol) and triethylamine (MW: 101.19, d: 0.726; 33.5 ml, 0.24 mol, 2.4 eq.) in anhydrous $CH_2Cl_2$ (100 ml) was added slowly, keeping the internal temperature below 5° C. At the end of the addition, stirring was continued for 30 min at 0° C. and then at room temperature over night (17.5 h). The reaction mixture was diluted with $CH_2Cl_2$ (500 ml), washed with sat. aq. $NaHCO_3$ (2×500 ml, 1×250 ml), water (2×300 ml), brine (250 ml), dried over $MgSO_4$, and concentrated under reduced pressure to give a highly viscous, amber oil. Ethanol (250 ml) was added, and the mixture was stirred until a solid formed. Additional ethanol (450 ml) was added, and the mixture was heated to 70° C. until a clear solution was obtained, which was allowed to cool to room temperature over night. The thick suspension (solvent not visible, voluminous product) was filtered, and the off-white precipitate was washed with ethanol, hexane, and dried under high vacuum. Yield: 34.10 g (70%), NMR purity >98% ($^1$H NMR).

EXAMPLE 3

Synthesis of Tethered (S,S)-MsDPEN

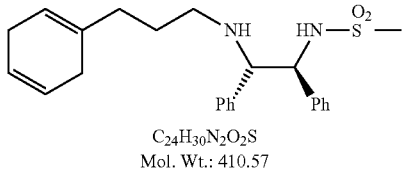

$C_{24}H_{30}N_2O_2S$
Mol. Wt.: 410.57

A solution of 3-(1,4-cyclohexadien-1-yl)-1-propanol (MW: 138.21; 8.3 g, 60.0 mmol, 1.20 eq.) and 2,6-lutidine (MW: 107.16, d: 0.92 g/ml; 8.3 ml, 70.0 mmol, 1.40 eq.) in anhydrous $CH_2Cl_2$ (250 ml) was cooled to 0° C. under $N_2$. A solution of triflic anhydride (MW: 281.14, d: 1.677; 10.7 ml, 62.5 mmol, 1.25 eq.) in anhydrous $CH_2Cl_2$ (40 ml) was added slowly, keeping the internal temperature below 5° C. The resulting amber solution was stirred for 30 min at 0° C., 90 min at room temperature, and cooled back to 0° C. A solution of (S,S)-MsDPEN (MW: 290.39; 14.52 g, 50.0 mmol) and triethylamine (MW: 101.19, d: 0.726; 11.2 ml, 80.0 mmol, 1.6 eq.) in anhydrous $CH_2Cl_2$ (90 ml) was added slowly, keeping the internal temperature below 5° C. At the end of the addition, stirring was continued for 30 min at 0° C. and then at room temperature over night (20.5 h). The reaction mixture was diluted with $CH_2Cl_2$ (total volume: ca. 500 ml), washed with sat. aq. $NaHCO_3$ (2×250 ml, 1×150 ml), water (2×200 ml), brine (200 ml), dried over $MgSO_4$, and concentrated under reduced pressure to give a highly viscous, amber oil (26.5 g). The crude product was filtered through a layer of silica gel (7 cm thick, 9 cm in diameter) with EtOAc/hexane 2/1 as eluent. The product was obtained with the first two fractions (200 ml each) but still contained an impurity, which eluted first (TLC in EtOAc, $R_f$(impurity): 0.76, $R_f$(tethered MsDPEN): 0.66; visualised with UV @ 254 nm or with basic $KMnO_4$). Evaporation of the solvents under reduced pressure yielded the crude product as a yellow-to-orange oil, which slowly solidified (20.2 g).

The solid was dissolved in MTBE (500 ml) and the solution was cooled to ca. 0° C. A 1.25 M solution of HCl in MeOH (120 ml, 150 mmol) was added with vigorous stirring. After 45 min at 0° C. the thick suspension was filtered, the solid was washed with MTBE, and dried under high vacuum. Yield: 17.13 g (77%), NMR purity >98% ($^1$H NMR).

A second batch of product was obtained by working up the mother liquor: The combined filtrate and washings were evaporated to dryness under reduced pressure until a solid was obtained, which was triturated with ethyl acetate (40 ml) at 70° C. for 1 hour. After cooling to room temperature, the mixture was filtered and the filter cake was washed with EtOAc. The off-white solid was then dried under high vacuum. Yield: 1.66 g (7%), NMR purity >98% ($^1$H NMR).

EXAMPLE 4

Synthesis of Ts-DPEN Ru Dimer

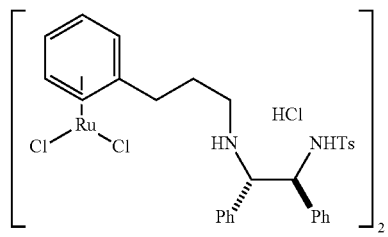

Procedure 1. To a stirred suspension of (R,R)-tethered-diamine (11.68 g, 24 mmol) in EtOH (500 mL) was added concentrated HCl (3 mL, 37%, 36 mmol) at 60° C. and solution stirred for 30 minutes. The solution was then heated to 75° C. and to this was added $RuCl_3$ in $H_2O$ (Assay 19.23% in Ru, 6.46 mL, 20 mmol) in EtOH (50 mL) added dropwise over 1 hour. The solution was then stirred at 75° C. overnight. The solution was then cooled, hexane (600 mL) added with vigorous stirring and solution filtered. The solids obtained were then washed with hexane, collected and dried under high vacuum to give a light brown solid (~15 g, carried forward). The isolated product was shown to be >95% pure by $^1$H NMR (CDCl$_3$). No further purification was attempted and this material was carried forward to the next step.

Procedure 2. To a stirred suspension of (R,R)-diamine (2.9 g, 6 mmol) in DCE (20 mL) was added HCl (3 mL, 37%, 36 mmol) at 50° C. and solution stirred for 30 minutes. The resulting suspension was then heated to 75° C. and to this was added $RuCl_3$ in $H_2O$ (Assay 19.23% in Ru, 1.62 mL, 5 mmol) in IPA (20 mL) added dropwise over 1 hour. The solution was then stirred at 75° C. overnight. The solution was then cooled, hexane (100 mL) added with vigorous stirring and solution filtered. The solids obtained were then washed with hexane, collected and dried under high vacuum to give a light brown solid (~6 g, carried forward). The dimer was isolated as a crude solid and shown to be >90% pure by $^1$H NMR (CDCl$_3$).

Procedure 3. To a stirred suspension of (R,R)-diamine (2.9 g, 6 mmol) in Toluene (20 mL) was added HCl (3 mL, 37%, 36 mmol) at 50° C. and the solution was stirred for 30 minutes. The resulting suspension was then heated to 75° C. and to this was added $RuCl_3$ in $H_2O$ (Assay 19.23% in Ru, 1.62 mL, 5 mmol) in IPA (20 mL) dropwise over 1 hour. The solution was then stirred at 75° C. overnight. The solution was then cooled, hexane (100 mL) added with vigorous stirring and solution filtered. The solids obtained were then washed with hexane, collected and dried under high vacuum to give a light brown solid (~6 g, carried forward). The dimer was isolated as a crude solid and shown to be >90% pure by $^1$H NMR (CDCl$_3$).

EXAMPLE 5

Synthesis of [Ts-teth-DPEN Ru Cl] (Monomer)

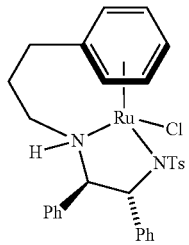

Procedure 1. To a stirred solution of the (R,R)-dimer (carried forward, ~20 mmol) in DCM (300 mL) at 0° C. was added N,N-diisopropylethylamine (20.9 mL, 120 mmol) and solution stirred at room temperature for 1 hour. The solution was then filtered over celite, IPA (300 mL) added and the DCM removed by rotary evaporation. The resulting suspension was then filtered and solid collected as a dark orange solid. The solid was then further dried under high vacuum overnight to give a fine orange powder (10.6 g, 83%). Isolated product was shown to be >95% pure by $^1$H NMR (CDCl$_3$).

Procedure 2. To a stirred solution of the (R,R)-dimer (14 g, ~20 mmol) in IPA (1 L) at 50° C. was added N,N-diisopropylethylamine (20.9 mL, 120 mmol) and solution stirred at 85° C. for 2 hours. The solution was then cooled, evaporated to a third of its original volume and then filtered to give a dark orange solid. The solid was then further dried under high vacuum over night to give a fine orange powder (8.5 g, 67%). Isolated product was shown to be >95% pure by $^1$H NMR (CDCl$_3$).

EXAMPLE 6

Synthesis of [Ts-teth-DPEN Ru Cl] One-Pot

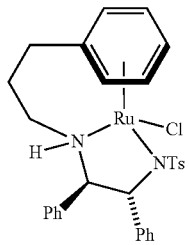

Procedure 1. To a stirred suspension of (R,R)-diamine (2.9 g, 6 mmol) in Toluene (20 mL) was added HCl (0.75 mL, 37%, 9 mmol) at 50° C. and solution stirred for 30 minutes. The resulting suspension was then heated to 75° C. and to this was added RuCl$_3$ in H$_2$O (Assay 19.23% in Ru, 1.62 mL, 5 mmol) in IPA (10 mL) added dropwise over 1 hour. The solution was then stirred at 75° C. overnight (16 h). The solution was then cooled to 0° C., toluene (30 mL) added and N,N-diisopropylethylamine (4.35 mL, 25 mmol) added dropwise with stirring. The solution was then allowed to warm to room temperature and then heated to 80° C. for 30 mins. The solution was then cooled, diluted with DCM (50 mL), filtered over neutral alumina (1 g/mmol) and pad washed with further portions of DCM (2×20 mL). The filtrate was evaporated to remove the DCM/toluene, IPA (50 mL) added and solution stirred at room temperature for 1 h. The resulting slurry was then filtered to give an orange solid, which was dried under high vacuum for 2 hours (2 g, 63%). No exotherm was observed at this scale, but care should be taken, as this could be possible at larger scale. After the initial heating phase a thick precipitate formed which resulted in the stirring of the solution failing. Addition of the toluene and Hunigs base however resulted in re-dissolution of the solids as the monomer formation proceeded. Isolated product was shown to be >95% pure by $^1$H NMR (CDCl$_3$).

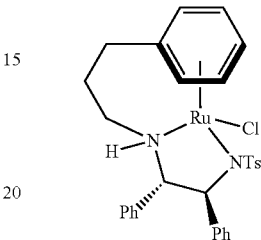

Procedure 2. To a stirred suspension of (S,S)-diamine (14.5 g, 30 mmol) in Toluene (100 mL) under nitrogen was added HCl (3.75 mL, 37%, 45 mmol) at 50° C. and solution stirred for 30 minutes. The resulting suspension was then heated to 75° C. and to this was added RuCl$_3$ in H$_2$O (Assay 19.23% in Ru, 8.1 mL, 25 mmol) in IPA (50 mL) added dropwise over 1 hour. The solution was then stirred at 75° C. overnight (16 h). The solution was then cooled to 0° C., DCM (100 mL) added and N,N-diisopropylethylamine (21.75 mL, 125 mmol) added dropwise with stirring. The solution was then allowed to warm to room temperature and then stirred for 2 h. The solution was then filtered over neutral alumina (1 g/mmol) and pad washed with further portions of 10% IPA/DCM (2×50 mL). The filtrate was evaporated to remove the DCM/toluene, IPA (200 mL) added and solution stirred at room temperature for 2 h. The resulting slurry was then filtered to give an orange solid, which was washed with cold IPA (30 mL) and dried under high vacuum for 2 hours (12.3 g, 77%). After the initial heating phase a thick precipitate formed which resulted in the stirring of the solution failing. Addition of the DCM and Hunigs base however resulted in re-dissolution of the solids as the monomer formation proceeded. Crude Isolated product was shown to be >95% pure by $^1$H NMR (CDCl$_3$). Further purification can be undertaken by dissolution with DCM (100 mL) and IPA (100 mL), followed by removal of the DCM by rotary evaporation. The resulting slurry could then be filtered as before and solids dried to give pure material.

EXAMPLE 7

Synthesis of [Ms-teth-DPEN Ru Cl] One-Pot

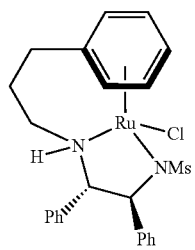

Procedure 1. To a stirred suspension of (S,S)-diamine.HCl (2.67 g, 6 mmol) in Toluene (20 mL) at 75° C. under nitrogen was added RuCl₃ in H₂O (Assay 19.23% in Ru, 1.62 mL, 5 mmol) in IPA (10 mL) dropwise over 1 hour. The solution was then stirred at 75° C. overnight (16 h). The solution was then cooled to 0° C., DCM (30 mL) added and N,N-diisopropylethylamine (4.35 mL, 25 mmol) added dropwise with stirring. The solution was then allowed to warm to room temperature and stirred for 2 h. The solution was then diluted with DCM (50 mL), filtered over neutral alumina (1 g/mmol) and pad washed with further portions of DCM (2×20 mL). The filtrate was evaporated to remove DCM/toluene, IPA (50 mL) added and solution stirred at room temperature for 1 h. The resulting slurry was then filtered to give an orange solid, which was dried under high vacuum for 2 hours (1.8 g, 64%); After the initial heating phase a thick precipitate was not observed in comparison to the Ts example. Isolated product was shown to be >95% pure by ¹H NMR (CDCl₃).

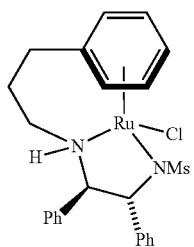

Procedure 2. To a stirred suspension of (R,R)-diamine.HCl (8.03 g, 18 mmol) in Toluene (60 mL) at 75° C. under nitrogen was added RuCl₃ in H₂O (Assay 19.23% in Ru, 4.86 mL, 15 mmol) in IPA (30 mL) dropwise over 1 hour. The solution was then stirred at 75° C. overnight (16 h). The solution was then cooled to 0° C., DCM (100 mL) added and N,N-diisopropylethylamine (15.66 mL, 90 mmol) added dropwise with stirring. The solution was then allowed to warm to room temperature and stirred for 2 h. The solution was then filtered over neutral alumina (1 g/mmol) and pad washed with further portions of 10% IPA/DCM (2×50 mL). The filtrate was evaporated to remove the DCM/toluene, IPA (200 mL) added and solution stirred at room temperature for 2 h. The resulting slurry was then filtered to give an orange solid, which was washed with cold IPA (30 mL) and dried under high vacuum for 2 hours (5.0 g, 60%); After the initial heating phase a thick precipitate was not observed in comparison to the Ts example. Crude Isolated product was shown to be >95% pure by ¹H NMR (CDCl₃). Further purification could be undertaken by dissolution with DCM (100 mL) and IPA (100 mL), followed by removal of the DCM by rotary evaporation. The resulting slurry could then be filtered as before and solids dried to give pure material.

EXAMPLE 8

Synthesis of Achiral Tethered Catalysts

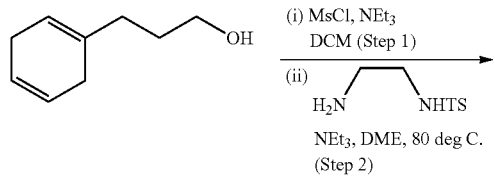

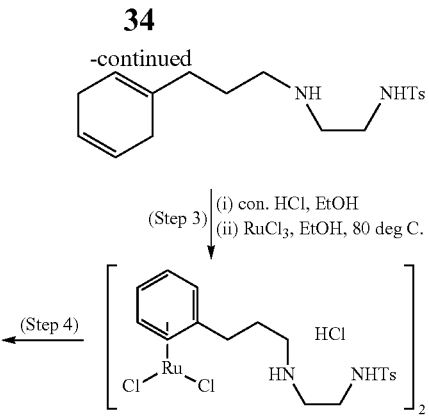

Synthesis of the Ligand (Steps 1 and 2)

To a stirred solution of 3-(1,4-cyclohexadien-1-yl)-1-propanol (MW: 138.21; 1.21 g, 9.18 mmol) in 25 mL of DCM 2.7 mL of NEt₃ (19.28 mmol) was added and cooled to 0° C. A solution of methane sulfonyl chloride (1.1 mL, 13.8 mmol) was added over a period of 20 min by keeping the internal temperature below 5° C. After 30 min the reaction mixture was allowed to warm up to RT and stirred overnight. The reaction was quenched with saturated NaHCO₃ solution. The reaction was worked up with water, brine and dried over Na₂SO₄. The mesylate derivative (96% yield) was isolated was carried forward to the next step. To a stirred solution of monotosylated ethylenediamine (1.98 g, 9.25 mmol) in 20 mL of 1,2-dimethoxy ethane and NEt₃ (2.7 mL, 19.43 mmol) at 60° C. a solution of the mesylate derivative in 10 mL of DME was added slowly over a period of 5 min. Then the solution was heated to 80° C. and stirred overnight. The reaction was quenched with saturated NaHCO₃ solution. The reaction was worked up with water, brine and dried over Na₂SO₄. The desired ligand was isolated by column chromatography with EtOAc as eluent (R_f value 0.1 in EtOAc; visualised with UV @ 254 nm or with basic KMnO₄). Isolated yield of the ligand was 1.0 g (33% based on the starting alcohol). ¹H NMR: (300 MHz, CDCl₃) 7.77-7.73 (2H, m, ArH), 7.32-7.27 (2H, m, ArH), 5.71 (2H, br s, CH=CH), 5.34 (2H, br s, =CH), 3.04-3.00 (2H, m, CH₂NH), 2.82-2.73 (2H, m, CH₂NH), 2.72-2.68 (2H, m, —CH₂C= or =CH—CH₂—CH=), 2.56-2.51 (4H, m, —CH₂C= or =CH—CH₂—CH=), 2.42 (3H, s, CH₃), 1.95-1.90 (2H, m, —NH—CH₂—), 1.53-1.48 (2H, m, —CH₂—CH₂—CH₂).

Synthesis of Dimer (Step 3)

To a stirred solution of tethered ethylenediamine ligand (MW: 334.17, 0.270 g, 0.808 mmol) in EtOH (15 mL) was added concentrated HCl (0.12 mL, 35%, 1.212 mmol) at 0° C. The solution was heated at 60° C. for 30 minutes. After this the solution was heated to 75° C. and a solution of RuCl₃ (0.110 g, 0.533 mmol) in EtOH (15 mL) and water (0.5 mL) added dropwise over 20 min. The solution was then stirred at 75° C. overnight. The solution was then cooled, hexane (60 mL) added with vigorous stirring and filtered. The solids obtained were then washed with hexane, collected and dried under high vacuum to give a dark brown solid (0.006 g). The filtrate was concentrated to give orange powder (0.040 g). Both these solids were combined for the next reaction. The isolated product was shown to be >95% pure by ¹H NMR: ¹H NMR (300 MHz, DMSO-d6) 8.50 (2H, br s, NH₂), 7.82 (2H, br s, NH), 7.71-7.68 (2H, m, ArH), 7.44-7.42 (2H, m, ArH), 6.02 (2H, br s, Ru—ArH), 5.79 (3H, br s, Ru—ArH), 2.98 (5 or 6 H, br s, CH₂), 2.30 (3H, s, CH₃), 1.92 (2H, br s, —CH₂—).

Synthesis of Monomer (Step 4)

To a stirred solution of the dimer (MW: 1081.80, 0.238 g, 0.220 mmol) in DCM (50 mL) at 0° C. was added N,N-diisopropylethylamine (3.0 mL, 1.696 mmol) and the solution was stirred at room temperature for 2 hours. The solution was then filtered over celite and the DCM was removed by rotary evaporation. EtOH was added to the resulting paste and stored in the freezer for 3 hours and the cold solution was filtered and an orange precipitate was collected. The dark precipitate was washed with further portions of cold EtOH. The desired ruthenium complex was isolated by column chromatography with EtOAc ($R_f$ value 0.2 in EtOAc; visualised with UV @ 254 nm and phosphomolybdic acid). $^1$H NMR (300 MHz, DMSO-d6) 7.68 (1H, br s, NH), 7.82 7.59 (2H, d, ArH), 7.13 (2H, d, ArH), 5.91 (1H, m, Ru—ArH), 5.79-5.71 (2H, m, Ru—ArH), 5.26-5.20 (2H, m, Ru—ArH), 2.29 (3H, s, $CH_3$).

EXAMPLE 9

Hydrogenation of Acetophenone Using Tethered-Ts/MsDPENRuCl Catalysts and Optional Additives

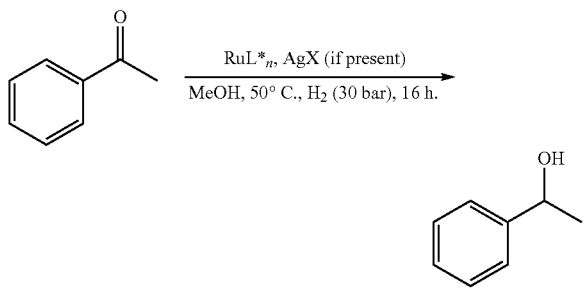

Experimental Procedure: Ru catalyst (1.2 mg, $1.9 \times 10^{-6}$ mol) and silver salt ($3.8 \times 10^{-6}$ mol) (if present) were weighed into a glass reaction tube. MeOH (3 mL) added, followed by acetophenone. The vessel was placed in a Biotage Endeavour and flushed with nitrogen, then hydrogen gas. The reaction was heated to 50° C. under 30 bar (450 PSI) $H_2$ for 16 hours and analysed by TLC and GC.

See Table 1 for the results of the hydrogenation experiments.

EXAMPLE 10

Hydrogenation of Acetophenone with [(R,R)-Ts-teth-DPEN Ru Cl] and [(S,S)-Ts-teth-DPEN Ru Cl]

Experimental Procedure: Ru catalyst (0.005 mol) weighed into a glass reaction tube. The vials were placed in a Biotage Endeavour and flushed with nitrogen. Acetophenone was added, followed by MeOH. The reaction was purged with hydrogen gas, heated and pressurised. The reaction was heated and pressurised with $H_2$ for 16 hours and analysed by GC.

See Table 2 for the results of the hydrogenation of acetophenone with [(R,R)-Ts-teth-DPEN Ru Cl]

See Table 3 for the results of the hydrogenation of acetophenone with [(S,S)-Ts-teth-DPEN Ru Cl]

EXAMPLE 11

Hydrogenation of Acetophenone: Comparative Experiments in MeOH

Experimental Procedure: Ru catalyst weighed into a glass reaction tube. The vials were placed in a Biotage Endeavour and flushed with nitrogen. Acetophenone was added, followed by MeOH (total reaction volume: 4 mL). The reaction was purged with hydrogen gas, heated and pressurised. The reaction was heated under 30 bar (435 psi) $H_2$ for 16 hours and analysed by and GC.

See Table 4 for the results of the comparative experiments.

As can be seen, the non-tethered catalyst is less active than the tethered catalyst when the catalyst loading was reduced to S/C 1000/1.

EXAMPLE 12

Hydrogenation of Acetophenone with Tethered TsEn-RU Catalyst

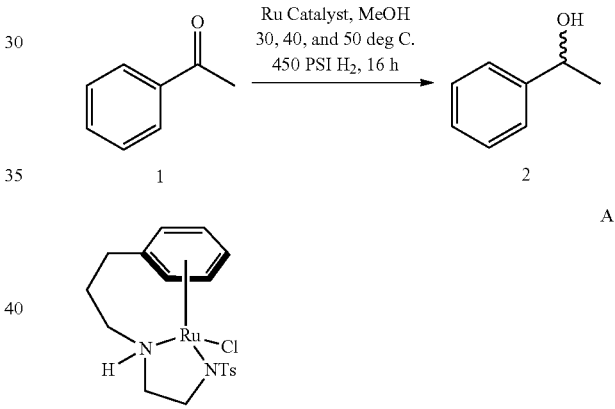

See Table 5 for the results of the hydrogenation of acetophenone with the tethered TsEn-Ru catalyst.

TABLE 1

| Expt | Catalyst | Substrate/Catalyst | AgX (mol %) | Conversion (%)[a] | Ee (%)[a] |
|---|---|---|---|---|---|
| 1 | Ts-DPEN Teth RuCl | 100/1 | — | 70 | 94 |
| 2 | Ts-DPEN Teth RuCl | 100/1 | AgOTf (2)[b] | 84 | 90 |
| 3 | Ts-DPEN Teth RuCl | 100/1 | $AgPF_6$ (2) | 16 | 87 |
| 4 | Ts-DPEN Teth RuCl | 100/1 | $AgBF_4$ (2) | 69 | 92 |
| 5 | Ts-DPEN Teth RuCl | 200/1 | AgOTf (1) | 80 | 94 |
| 6 | Ts-DPEN Teth RuCl | 400/1 | AgOTf (0.5) | 63 | 92 |
| 7 | Ts-DPEN Teth RuCl | 100/1 | TfOH (2) | 24 | 90 |
| 8 | Ms-DPEN Teth RuCl | 100/1 | — | 38 | 82 |
| 9 | Ms-DPEN Teth RuCl | 100/1 | AgOTf (2) | 94 | 92 |
| 10 | Ms-DPEN Teth RuCl | 100/1 | $AgPF_6$ (2) | 41 | 92 |
| 11 | Ms-DPEN Teth RuCl | 100/1 | $AgBF_4$ (2) | 25 | 84 |

[a] Determined by GC.
[b] —OTf is trimethanesulfonate.

TABLE 2 hydrogenation of acetophenone with [(R,R)-Ts-teth-DPEN Ru Cl]

| Expt. | S/C | Solv. | Scale [S] | Press. | Temp. | Time | Alcohol (%)[a] | ee (%)[a] |
|---|---|---|---|---|---|---|---|---|
| 12 | 200/1 | MeOH | 1 mmol [0.5 M] | 30 bar | 50° C. | 16 h | >99% | 95% (R) |
| 13 | 250/1 | MeOH | 1 mmol [0.4 M] | 30 bar | 50° C. | 16 h | >99% | 94.5% (R) |
| 14 | 500/1 | MeOH | 2 mmol [0.5 M] | 30 bar | 50° C. | 16 h | 67% | 92.5% (R) |
| 15 | 500/1 | MeOH | 2 mmol [0.5 M] | 30 bar | 60° C. | 16 h | >99% | 94.5% (R) |
| 16 | 500/1 | MeOH | 10 mmol [1 M] | 15 bar | 60° C. | 24 h | 97% | 91.5% (R) |

[a]Determined by GC (ChromPack CP-Chirasil-Dex-CB 25 m × 0.25 mm × 0.25 μm. 100° C. for 10 min, then to 200° C. @ 10° C./min, 10 psi He flow, injector: 200° C.; detector (FID): 210° C.

TABLE 3 hydrogenation of acetophenone with [(S,S)-Ts-teth-DPEN Ru Cl]

| Expt. | S/C | Solv. | Scale [S] | Press. | Temp. | Time | Alcohol (%)[a] | ee (%)[a] |
|---|---|---|---|---|---|---|---|---|
| 17 | 100/1 | MeOH | 2 mmol [0.5 M] | 30 bar | 40° C. | 16 h | 100% | 94% (S) |
| 18 | 250/1 | MeOH | 2 mmol [0.5 M] | 30 bar | 50° C. | 16 h | 100% | 94% (S) |
| 19 | 500/1 | MeOH | 2 mmol [0.5 M] | 30 bar | 60° C. | 16 h | 100% | 93.5% (S) |
| 20 | 1000/1 | MeOH | 2 mmol [0.5 M] | 30 bar | 60° C. | 16 h | 100% | 93% (S) |
| 21 | 2000/1 | MeOH | 4 mmol [1 M] | 30 bar | 60° C. | 16 h | 49% | 93% (S) |

[a]Determined by GC (ChromPack CP-Chirasil-Dex-CB 25 m × 0.25 mm × 0.25 μm. 100° C. for 10 min, then to 200° C. @ 10° C./min, 10 psi He flow, injector: 200° C.; detector (FID): 210° C.

TABLE 4 hydrogenation of acetophenone: comparative experiments in MeOH

| Expt. | S/C | Catalyst | Scale [S] | Press. | Temp. | Time | Alcohol (%)[a] | ee (%)[a] |
|---|---|---|---|---|---|---|---|---|
| 22 | 100/1 | [(S,S)Ts-teth-DPEN Ru Cl] | 2 mmol [0.5 M] | 30 bar | 40° C. | 16 h | >99% | 94% (S) |
| 22 (Comparative) | 100/1 | [(S,S)-TsDPEN Ru(p-cym)Cl] | 2 mmol [0.5 M] | 30 bar | 40° C. | 16 h | >99% | 92% (S) |
| 23 | 500/1 | [(S,S)Ts-teth-DPEN Ru Cl] | 2 mmol [0.5 M] | 30 bar | 60° C. | 16 h | >99% | 93.5% (S) |
| 23 (Comparative) | 500/1 | [(S,S)-TsDPEN Ru(p-cym)Cl] | 2 mmol [0.5 M] | 30 bar | 60° C. | 16 h | >99% | 93.5% (S) |
| 24 | 1000/1 | [(S,S)Ts-teth-DPEN Ru Cl] | 2 mmol [0.5 M] | 30 bar | 60° C. | 16 h | >99% | 94% (S) |
| 24 (Comparative) | 1000/1 | [(S,S)-TsDPEN Ru(p-cym)Cl] | 2 mmol [0.5 M] | 30 bar | 60° C. | 16 h | 77% | 93% (S) |

[a]Determined by GC (ChromPack CP-Chirasil-Dex-CB 25 m × 0.25 mm × 0.25 μm. 100° C. for 10 min, then to 200° C. @ 10° C./min, 10 psi He flow, injector: 200° C.; detector (FID): 210° C.

TABLE 5

Hydrogenation of acetophenone with Ru catalyst A.[a]

| Expt. | Catalyst | S/C (molar ratio) | Temperature (° C.) | Conv. to 2 (%) |
|---|---|---|---|---|
| 25 | [Ts-teth-EN Ru Cl] | 100 | 30 | 100 |
| 26 | [Ts-teth-EN Ru Cl] | 250 | 40 | 100 |
| 27 | [Ts-teth-EN Ru Cl] | 1000 | 50 | 50 |

[a]Reaction conditions: Endeavor catalyst screening system; Catalyst, 1 (3.0 mmol), MeOH (1.0 ml/mmol), 31 bar H$_2$, 16 h.
[b]Analysed by GC (Column: CP-Sil 5 CB, 30 m, 0.25 mm, 1 μm).

The invention claimed is:

1. A process for the preparation of a compound of formula (VIII):

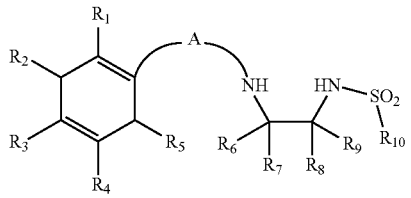

(VIII)

comprising the steps of:
a) converting a compound of formula (IX) into a compound of formula (X):

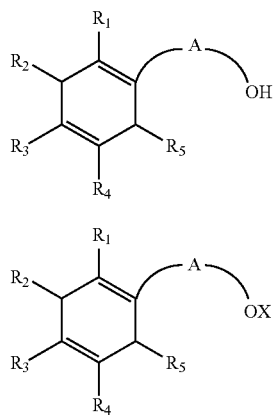

(IX)

(X)

b) reacting the compound of formula (X) with a compound of formula (XI) in a solvent to form the compound of formula (VIII):

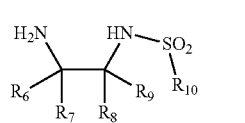

(XI)

wherein,
$R_1$, $R_2$, $R_3$, $R_4$ and $R_5$ are each independently selected from the group consisting of hydrogen, optionally substituted straight, branched or cyclic $C_{1-20}$ alkyl, optionally substituted straight, branched or cyclic $C_{1-20}$ alkoxy, optionally substituted $C_{6-20}$ aryl, optionally substituted $C_{6-20}$ aryloxy, —OH, —CN, —NR$_{20}$R$_{21}$, —COOH, COOR$_{20}$, —CONH$_2$, —CONR$_{20}$R$_{21}$ and —CF$_3$, wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —NR$_{30}$R$_{31}$, —COOR$_{30}$, —CONR$_{30}$R$_{31}$ and —CF$_3$; or $R_3$ and $R_4$ together form an aromatic ring composed of 6 to 10 carbon atoms which is optionally substituted with one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —NR$_{20}$R$_{21}$, —COOR$_{20}$, —CONR$_{20}$R$_{21}$ and —CF$_3$;

$R_6$, $R_7$, $R_8$ and $R_9$ are each independently selected from the group consisting of hydrogen, optionally substituted straight, branched or cyclic $C_{1-20}$ alkyl, optionally substituted straight, branched or cyclic $C_{1-20}$ alkoxy, optionally substituted $C_{6-20}$ aryl and optionally substituted $C_{6-20}$ aryloxy wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —NR$_{20}$R$_{21}$ —COOR$_{20}$, —CONR$_{20}$R$_{21}$ and —CF$_3$, or $R_6$ and $R_7$ together with the carbon atom to which they are bound and/or $R_8$ and $R_9$ together with the carbon atom to which they are bound form an optionally substituted $C_{3-20}$ cycloalkyl or an optionally substituted $C_{2-20}$ cycloalkoxy, wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —NR$_{20}$R$_{21}$, —COOR$_{20}$, —CONR$_{20}$R$_{21}$, and —CF$_3$, or one of $R_6$ and $R_7$ and one of $R_8$ and $R_9$ together form an optionally substituted $C_{5-10}$ cycloalkyl or an optionally substituted $C_{5-10}$ cycloalkoxy, wherein the substituents are independently selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN, —NR$_{20}$R$_{21}$, —COOR$_{20}$, —CONR$_{20}$R$_{21}$ and —CF$_3$;

$R_{10}$ is an optionally substituted straight, branched or cyclic $C_{1-10}$alkyl, an optionally substituted $C_{6-10}$ aryl or —NR$_{11}$R$_{12}$ wherein the substituents are selected from the group consisting of one or more straight, branched or cyclic $C_{1-10}$ alkyl, straight, branched or cyclic $C_{1-10}$ alkoxy, $C_{6-10}$ aryl, $C_{6-10}$ aryloxy, —Hal, —OH, —CN, —NR$_{20}$R$_{21}$, —COOR$_{20}$, —CONR$_{20}$R$_{21}$ and CF$_3$;

further wherein
$R_{11}$ and $R_{12}$ are independently selected from the group consisting of hydrogen, optionally substituted straight, branched or cyclic $C_{1-10}$ alkyl and optionally substituted $C_{6-10}$ aryl, wherein the substituents are selected from the group consisting of one or more straight, branched or cyclic $C_{1-10}$ alkyl groups, straight, branched or cyclic $C_{1-10}$ alkoxy, $C_{6-10}$aryl, $C_{6-10}$ aryloxy, —OH, —CN, —NR$_{20}$R$_{21}$, —COOR$_{20}$, —CONR$_{20}$R$_{21}$ and —CF$_3$, or $R_{11}$ and $R_{12}$ together with the nitrogen atom to which they are bound form an optionally substituted $C_{2-10}$ cycloalkyl-amino group wherein the substituents are selected from the group consisting of one or more straight, branched or cyclic $C_{1-10}$ alkyl, straight, branched or cyclic $C_{1-10}$ alkoxy, $C_{6-10}$ aryl, $C_{6-10}$ aryloxy, —OH, —CN, —NR$_{20}$R$_{21}$, —COOR$_{20}$, —CONR$_{20}$R$_{21}$ and —CF$_3$; $R_{20}$ and $R_{21}$ are independently selected from the group consisting of hydrogen, optionally substituted straight, branched or cyclic $C_{1-20}$ alkyl, optionally substituted straight, branched or cyclic $C_{1-20}$ alkoxy, optionally substituted $C_{6-20}$ aryl, optionally substituted $C_{6-20}$ aryloxy, OH, —CN, —NR$_{30}$R$_{31}$, —COOR$_{30}$, —CONR$_{30}$R$_{31}$ and —CF$_3$, wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN and —CF$_3$;

$R_{30}$ and $R_{31}$ are independently selected from the group consisting of hydrogen, optionally substituted straight, branched or cyclic $C_{1-20}$ alkyl, optionally substituted straight, branched or cyclic $C_{1-20}$ alkoxy, optionally substituted $C_{6-20}$ aryl, optionally substituted $C_{6-20}$ aryloxy, OH, —CN and —CF$_3$, wherein the substituents are selected from the group consisting of one or more straight, branched or cyclic $C_{1-20}$ alkyl, straight, branched or cyclic $C_{1-20}$ alkoxy, $C_{6-20}$ aryl, $C_{6-20}$ aryloxy, —OH, —CN and —CF$_3$;

and

A is an optionally substituted straight- or branched-chain $C_{3-5}$ alkyl wherein the substituents are selected from the group consisting of one or more straight, branched or cyclic $C_{1-10}$ alkyl, straight, branched or cyclic $C_{1-10}$ alkoxy, $C_{6-10}$ aryl and $C_{6-10}$ aryloxy, or A is a group of formula (II):

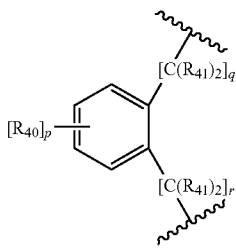

(II)

wherein p is an integer selected from 1, 2, 3 or 4;

each $R_{40}$ is independently selected from the group consisting of straight, branched or cyclic $C_{1-20}$ alkyl, straight, branched or cyclic $C_{1-20}$ alkoxy, $C_{6-20}$ aryl, $C_{6-20}$ aryloxy, —OH, —CN and —$CF_3$;

q and r are independently integers selected from 0, 1, 2 or 3 wherein q+r =1, 2 or 3;

each $R_{41}$ is independently selected from the group consisting of hydrogen, straight, branched or cyclic $C_{1-20}$ alkyl, straight, branched or cyclic $C_{1-20}$ alkoxy, $C_{6-20}$ aryl, $C_{6-20}$ aryloxy, —OH, —CN and —$CF_3$; and Hal is a halogen, and X is an electrophilic group c) reacting the compound of formula (VIII) with an acid HZ, where Z is an anion; and d) reacting the acid addition salt of the compound of formula (VIII) with a Ru(Hal)$_n$ complex, where Hal is a halogen and n is a number equal to or less than the coordination number of Ru, to form a complex of formula (XIII):

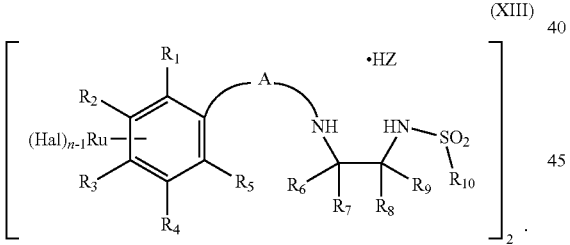

(XIII)

wherein the acid addition salt of the compound of formula (VIII) is prepared without isolation before reaction with the Ru(Hal)$_n$ complex.

2. A process according to claim 1, wherein step (a) comprises reacting the compound of formula (IX) with a base and a compound of formula (XII):

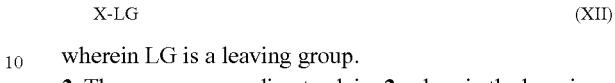

wherein LG is a leaving group.

3. The process according to claim 2, wherein the base is an amine.

4. The process according to claim 3, wherein the base is selected from the group consisting of lutidine and triethylamine.

5. The process according to claim 2, wherein the compound of formula (XII) is selected from the group consisting of trifluoromethane sulfonic anhydride, trifluoromethane sulfonic acid, methanesulfonyl chloride and p-toluenesulfonyl chloride.

6. The process according to claim 1, wherein step (b) further comprises a base.

7. The process according to claim 6, wherein the base is an amine.

8. The process according to claim 7, wherein the base is triethylamine.

9. The process according to claim 1, further comprising the step of treating the complex of formula (XIII) with a base to form the complex of formula (I):

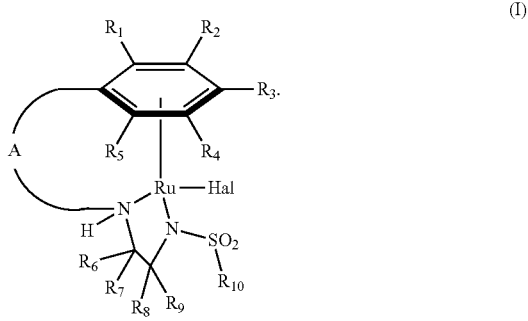

(I)

10. The process according to claim 1, wherein the complex of formula (XIII) is isolated.

* * * * *